United States Patent
McJames et al.

(10) Patent No.: US 9,585,988 B2
(45) Date of Patent: *Mar. 7, 2017

(54) ANCHORAGE DEVICES COMPRISING AN ACTIVE PHARMACEUTICAL INGREDIENT

(75) Inventors: William McJames, Hillsborough, NJ (US); Frank Do, Jersey City, NJ (US); Satish Pulapura, Bridgewater, NJ (US); Qing Ge, Solon, OH (US)

(73) Assignee: TYRX, Inc., Monmouth Junction, NJ (US)

(*) Notice: Subject to any disclaimer, the term of this patent is extended or adjusted under 35 U.S.C. 154(b) by 99 days.

This patent is subject to a terminal disclaimer.

(21) Appl. No.: 13/293,816

(22) Filed: Nov. 10, 2011

(65) Prior Publication Data

US 2012/0185004 A1    Jul. 19, 2012

Related U.S. Application Data

(60) Provisional application No. 61/413,135, filed on Nov. 12, 2010.

(51) Int. Cl.
*A61N 1/05* (2006.01)
*A61L 31/08* (2006.01)
(Continued)

(52) U.S. Cl.
CPC ............. *A61L 31/08* (2013.01); *A61L 31/10* (2013.01); *A61L 31/16* (2013.01); *A61N 1/059* (2013.01); *A61L 2300/602* (2013.01)

(58) Field of Classification Search
CPC ......... A61F 2/90; A61N 1/375; A61N 1/0558; A61N 1/057; A61N 1/059
(Continued)

(56) References Cited

U.S. PATENT DOCUMENTS

| 4,298,997 A | 11/1981 | Rybka |
| 4,326,532 A | 4/1982 | Hammar |

(Continued)

FOREIGN PATENT DOCUMENTS

| JP | 07-000430 A | 1/1995 |
| JP | 2000-512519 A | 9/2000 |

(Continued)

OTHER PUBLICATIONS

International Search Report and Written Opinion, PCT/US11/60197, dated Mar. 2, 2012.
(Continued)

*Primary Examiner* — Eric D. Bertram
(74) *Attorney, Agent, or Firm* — Sorell Lenna & Schmidt, LLP

(57) ABSTRACT

An anchorage device comprising a mesh substrate coupled to an implantable medical device is disclosed, where the mesh substrate has a coating comprising a polymer, and the mesh further comprises at least one active pharmaceutical ingredient. The active pharmaceutical agent is designed to elute from the mesh over time. The mesh substrate can be configured to reduce the mass of the anchorage device such that tissue in-growth and/or scar tissue formation at the treatment site is reduced. In some embodiments, the mesh substrate can be formed with a mesh having a low areal density. In some embodiments, the mesh substrate can include one or more apertures or pores to reduce the mass of the substrate.

50 Claims, 16 Drawing Sheets

(51) Int. Cl.
*A61L 31/10* (2006.01)
*A61L 31/16* (2006.01)

(58) Field of Classification Search
USPC .................................................. 607/3
See application file for complete search history.

(56) References Cited

U.S. PATENT DOCUMENTS

| | | | |
|---|---|---|---|
| 5,216,115 | A | 6/1993 | Kohn et al. |
| 5,217,493 | A | 6/1993 | Raad et al. |
| 5,614,284 | A | 3/1997 | Kranzler et al. |
| 5,676,146 | A | 10/1997 | Scarborough |
| 6,120,491 | A | 9/2000 | Kohn et al. |
| 6,548,569 | B1 | 4/2003 | Williams et al. |
| 6,656,488 | B2 | 12/2003 | Yi et al. |
| 6,838,493 | B2 | 1/2005 | Williams et al. |
| 6,887,270 | B2 | 5/2005 | Miller et al. |
| 6,981,944 | B2 | 1/2006 | Jamiolkowski et al. |
| 7,879,100 | B2 * | 2/2011 | Denoziere ............. A61F 2/3094 623/17.11 |
| 8,315,700 | B2 * | 11/2012 | Citron et al. .................... 607/5 |
| 2002/0072694 | A1 | 6/2002 | Snitkin et al. |
| 2002/0077701 | A1 * | 6/2002 | Kuslich ................... A61F 2/441 623/17.12 |
| 2003/0091609 | A1 | 5/2003 | Hendriks |
| 2003/0153983 | A1 | 8/2003 | Miller et al. |
| 2004/0147688 | A1 | 7/2004 | Kemnitzer et al. |
| 2004/0172048 | A1 | 9/2004 | Browning |
| 2004/0186529 | A1 | 9/2004 | Bardy et al. |
| 2004/0209538 | A1 * | 10/2004 | Klinge ................ A61B 3/1015 442/59 |
| 2005/0008671 | A1 | 1/2005 | Van Antwerp |
| 2005/0052466 | A1 | 3/2005 | Frazer et al. |
| 2005/0101692 | A1 | 5/2005 | Sohier et al. |
| 2005/0118227 | A1 | 6/2005 | Kohn et al. |
| 2005/0143817 | A1 | 6/2005 | Hunter et al. |
| 2005/0147690 | A1 | 7/2005 | Masters et al. |
| 2005/0149157 | A1 | 7/2005 | Hunter et al. |
| 2005/0161859 | A1 | 7/2005 | Miller et al. |
| 2005/0163821 | A1 | 7/2005 | Sung et al. |
| 2005/0177225 | A1 | 8/2005 | Hunter et al. |
| 2005/0208664 | A1 | 9/2005 | Keegan et al. |
| 2005/0209664 | A1 | 9/2005 | Hunter et al. |
| 2005/0228471 | A1 | 10/2005 | Williams et al. |
| 2006/0025852 | A1 | 2/2006 | Armstrong et al. |
| 2006/0034769 | A1 | 2/2006 | Kohn et al. |
| 2006/0052466 | A1 | 3/2006 | Handa |
| 2006/0147492 | A1 | 7/2006 | Hunter et al. |
| 2006/0246103 | A1 | 11/2006 | Ralph et al. |
| 2007/0179621 | A1 * | 8/2007 | McClellan, III ........ A61F 2/442 623/17.16 |
| 2007/0198040 | A1 | 8/2007 | Buevich et al. |
| 2007/0213416 | A1 | 9/2007 | Handa et al. |
| 2007/0286928 | A1 | 12/2007 | Sarmas et al. |
| 2008/0132922 | A1 | 6/2008 | Buevich et al. |
| 2009/0018559 | A1 * | 1/2009 | Buevich et al. ............. 606/151 |
| 2009/0029961 | A1 | 1/2009 | Modak et al. |
| 2009/0149568 | A1 | 6/2009 | Pacetti |
| 2010/0074940 | A1 | 3/2010 | Schwartz et al. |
| 2010/0129417 | A1 | 5/2010 | Moses et al. |
| 2010/0168808 | A1 * | 7/2010 | Citron ................... A61L 31/10 607/5 |

FOREIGN PATENT DOCUMENTS

| | | |
|---|---|---|
| JP | 2002-500065 A | 1/2002 |
| JP | 2002-522112 A | 7/2002 |
| JP | 2004-524059 A | 8/2004 |
| JP | 2004-535866 A | 12/2004 |
| JP | 2005-152651 A | 6/2005 |
| JP | 2007500552 A | 1/2007 |
| WO | 9747254 A1 | 12/1997 |
| WO | 9924107 A1 | 5/1999 |
| WO | 9934750 A1 | 7/1999 |
| WO | 2004071485 A1 | 8/2004 |
| WO | 2005/011767 A1 | 2/2005 |
| WO | 2006133569 A1 | 12/2006 |
| WO | 2007056134 A2 | 5/2007 |
| WO | 2008137807 A1 | 11/2008 |
| WO | 2009113972 A2 | 9/2009 |
| WO | 2010006046 A1 | 1/2010 |
| WO | 2010141475 A1 | 12/2010 |

OTHER PUBLICATIONS

Areolar Tissue, The Free Dictionary, May 2011.
Australian Examination Report for Application No. 2007344645 dated Mar. 8, 2012.
Canadian Office Action for Application No. 2,667,867 dated Aug. 19, 2013.
Canadian Office Action for Application No. CA/2667873 dated Feb. 11, 2013.
Darouiche, NEJM, 340, 1999.
Enhancing Medical Devices, Sep. 2005, <URL: http://www.tyrx.com/Collateral/documents/TyRx%20English-US/03-06-pr.pdf>.
Extended European Search Report for Application No. 07873600 dated Augus 30, 2012.
Extended European Search Report for Application No. EP07874257 dated Aug. 29, 2012.
Furacin, 2013 (obtained from http://www.drugs.com/cons/furacin-topical.html).
Greca, Hernia, 5, 2001.
Green, Clinical Cornerstone, vol. 3, 2001.
Japanese Office Action for Application No. 2009-535509 dated Apr. 15, 2013.
Japanese Office Action for Application No. 2010-502992 dated Apr. 17, 2013.
Japanese Office Action for Application No. 2009-535508 dated Aug. 14, 2012.
New product introduction at Tyrx Pharma, Inc. The Journal of Product and Brand management, US, Dec. 1, 2006, p. 468-472 The publication date has been recognized based on the description in http://www.ingentaconnect.com/content/mcb/096/2006/00000015/00000007/art00008, "Publication date: Dec. 1, 2006"[Date of Search Apr. 16, 2012].
Parsonnet, Pacing and Clinical Electrophysiology, 17, 1994.
Prevent, WordNet, 2011.
Rupp, Clinical Infectious Diseases, vol. 19, 1994.
TyRx Pharama, Inc., TyRx Press Releases, TyRx Announces FDA 510(k) Filing for New Antibiotic Eluting Surgical Mesh, USA, Jan. 17, 2006, [searched on May 2, 2012] URL, http://www.tyrx.com/Collateral/Documents/TyRx%20English-US/01-17-06-pr.pdf.
TyRx Pharama, Inc., TyRx Press Releases, TyRx Announces FDA 510(k) Filing for New Surgical Mesh, USA, May 17, 2005, [searched on May 2, 2012], URL, http://www.tyrx.com/Collateral/Documents/TyRx%20English-US/10-17-05-pr.pdf.
TyRx Pharama, Inc., TyRx Press Releases, TyRx Pharama's Anesthetic Coated Surgical Mesh Combination Product Assigned to "Device" Center at FDA, USA, Jan. 9, 2006, [searched on May 2, 2012], URL, http://www.tyrx.com/Collateral/Documents/TyRx%20English-US/01-09-06-pr.pdf.
TYRX Pharma, Inc. Announces Submission of a Premarket Application for PIVIT CRM, TYRX Press Releases [searched on Apr. 16, 2012], USA, Oct. 16, 2006, URL, http://www.tyrx.com/Collateral/Documents/TyRx%20English-US/10-16-06-pr.pdf.
Zoll, Annals of Surgery, Sep. 1964.
International Search Report and Written Opinion for Application No. PCT/US2011/049140 dated Aug. 27, 2012.
IP Australia Patent Examination Report No. 3, dated May 27, 2015, of Patent Application No. 2011326417 filed Nov. 12, 2010 (Assignee: TyRx, Inc.) issued by Australian Government IP Office.
Australia Patent Office, Patent Examination Report No. 1, Patent Application No. 2015264956, Applicants: TyRx, Inc., Mailed May 5, 2016.

* cited by examiner

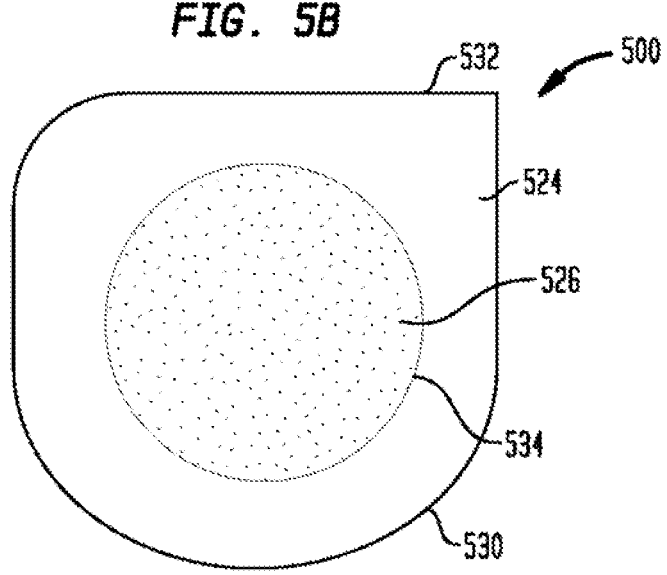

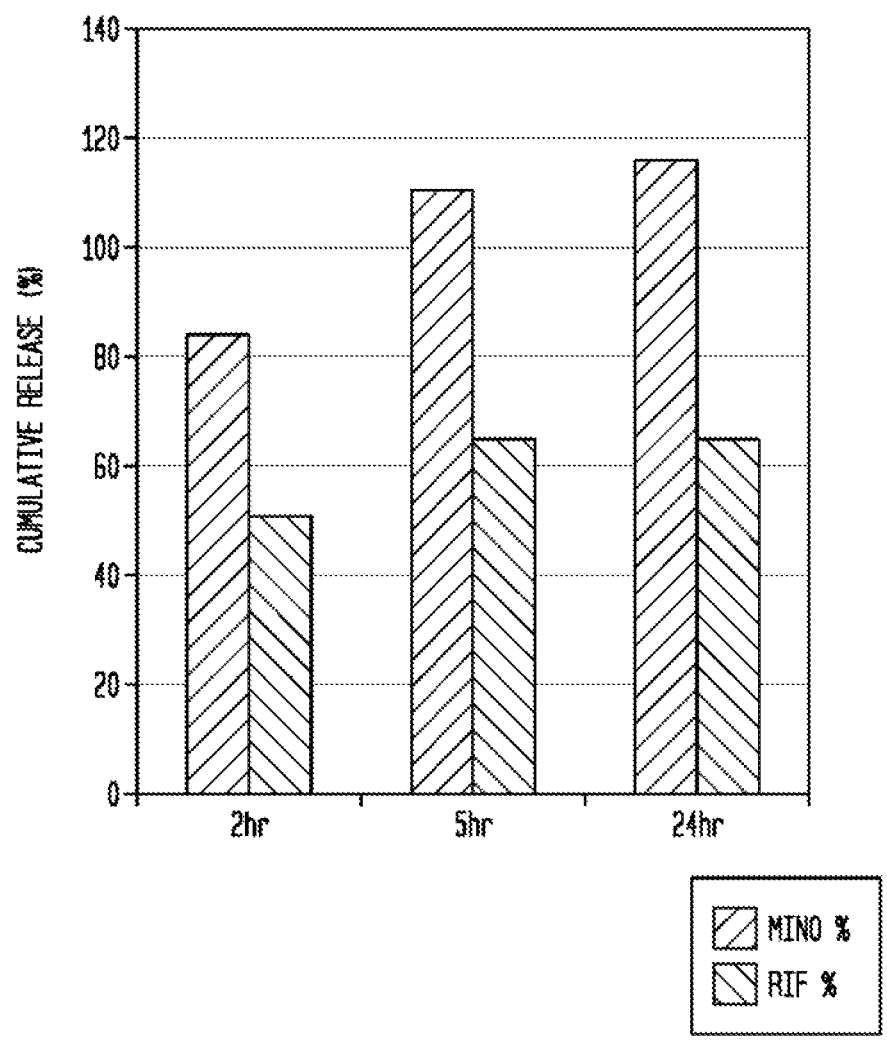

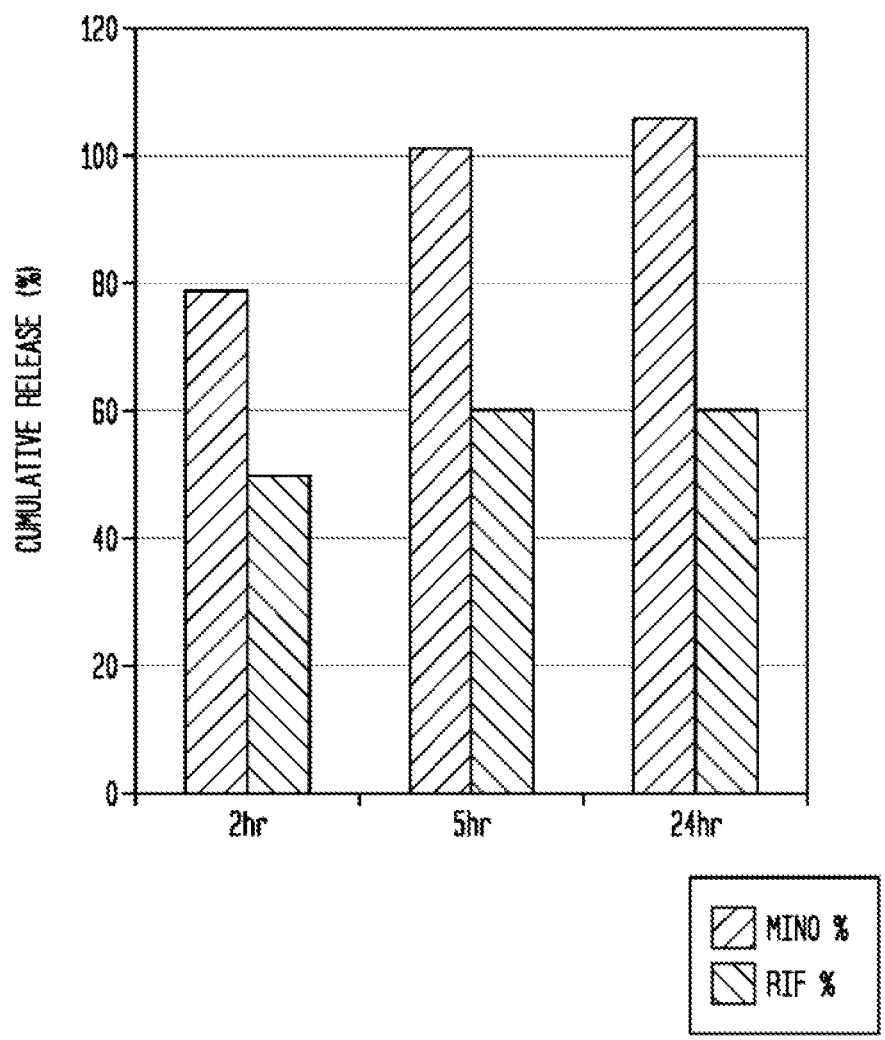

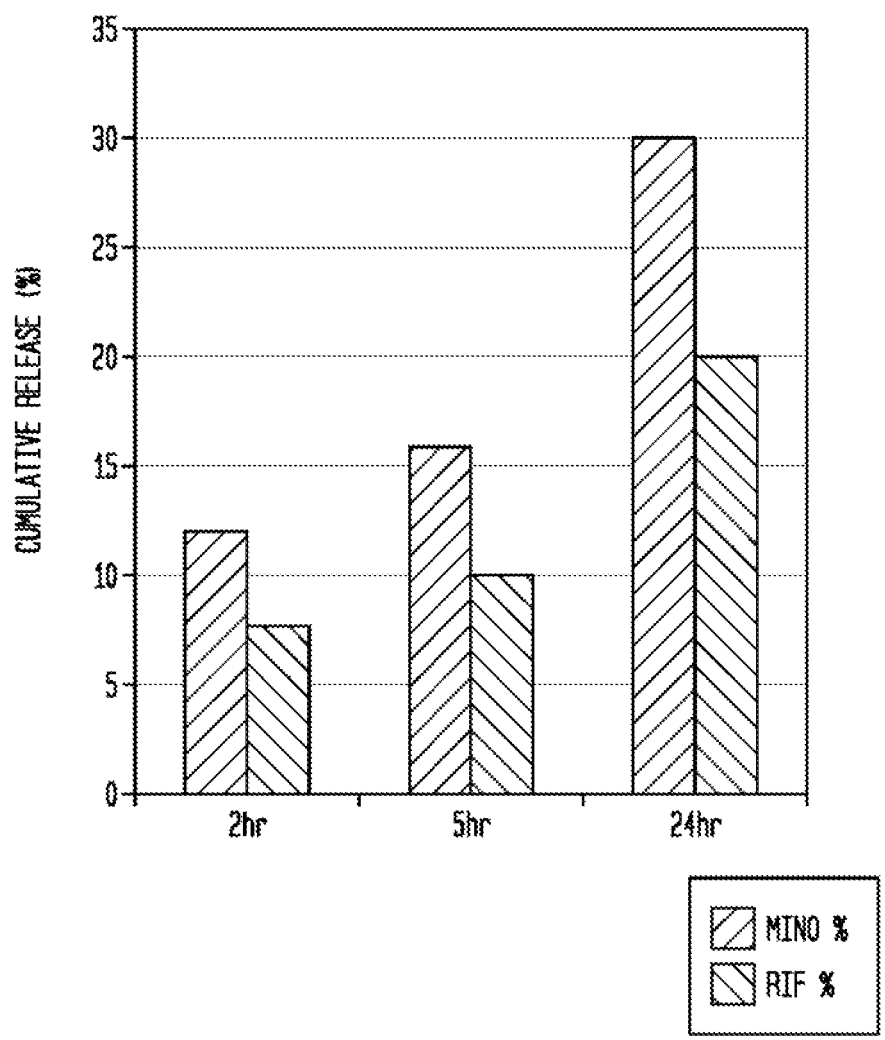

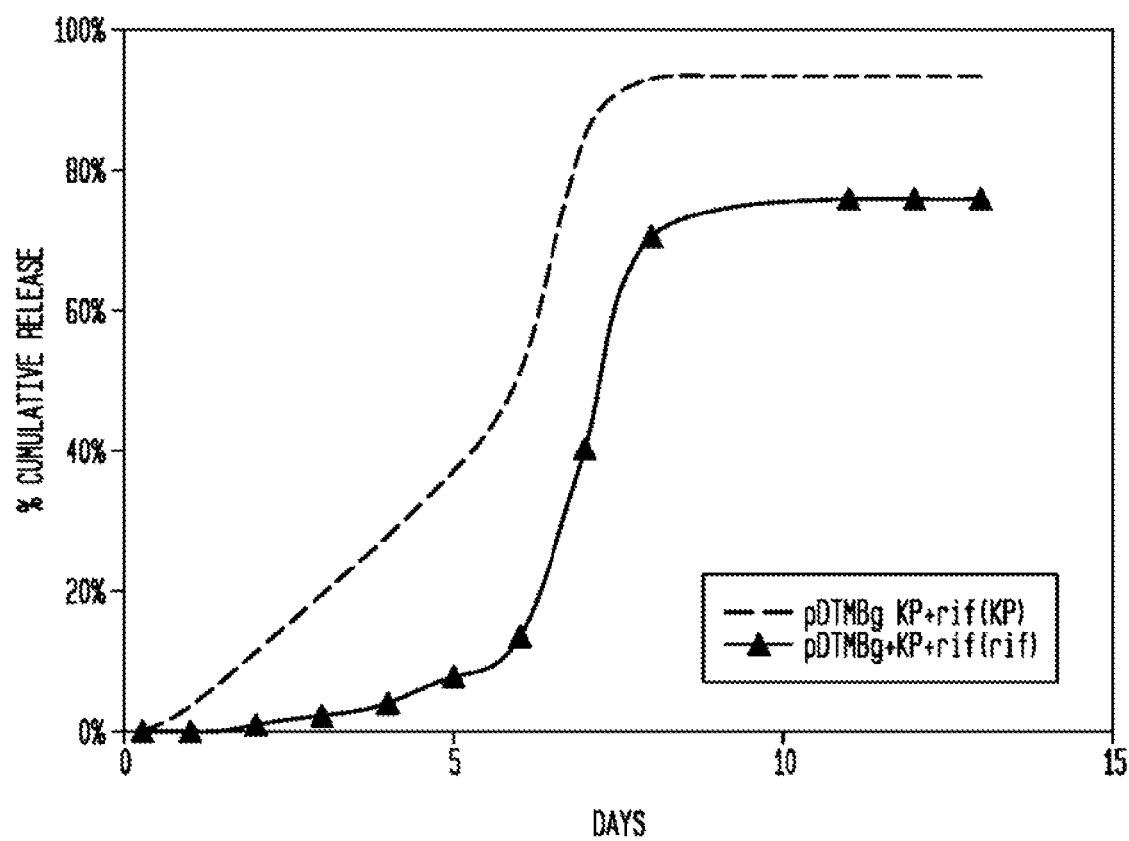

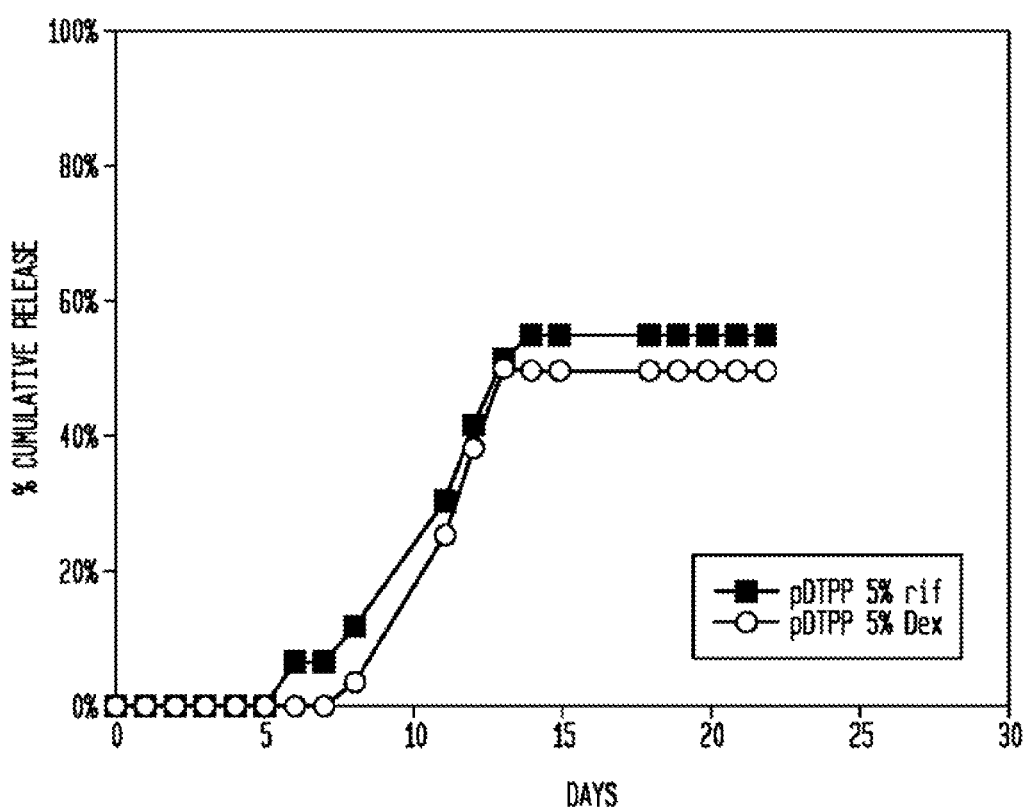

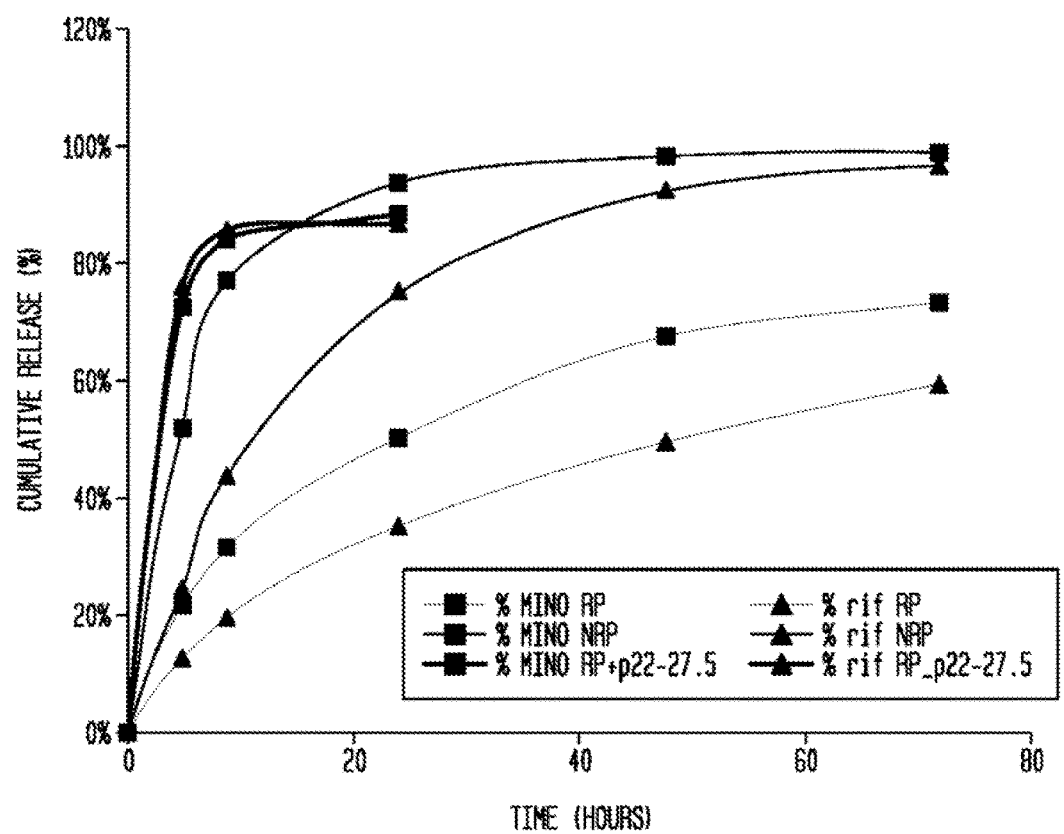

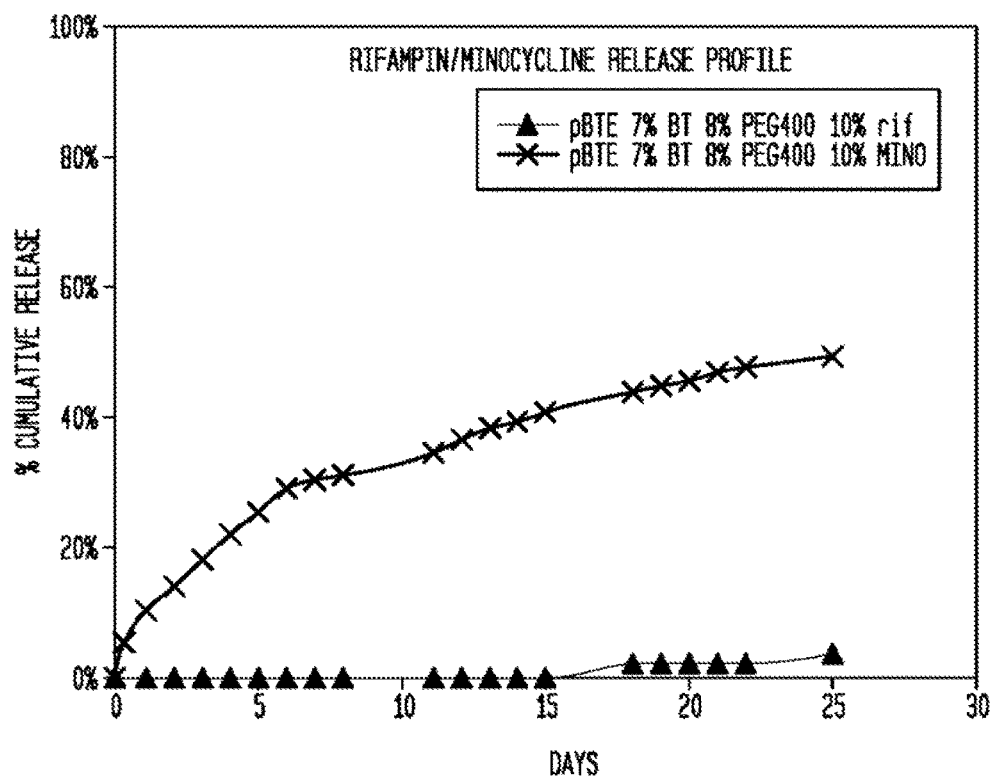

ANCHORAGE DEVICES COMPRISING AN ACTIVE PHARMACEUTICAL INGREDIENT

CROSS-REFERENCE TO RELATED APPLICATIONS

The present application claims the benefit of the filing date of U.S. Provisional Application No. 61/413,135, filed Nov. 12, 2010, entitled Devices And Methods For Anchoring A Medical Device Within A Body, which is hereby incorporated herein by reference.

BACKGROUND OF THE INVENTION

The invention relates generally to devices and methods for anchoring an implantable medical device within a body, where the anchorage device further comprises at least one API which is eluted over time.

Some known anchorage devices used to secure an implantable medical device within a body of a patient can include a mesh structure that forms a pocket or pouch in which an implantable medical device, such as, for example, an implantable cardiac rhythmic management device (e.g., an implantable cardiac pulse generator or defibrillator) can be disposed. The anchoring structure and implantable medical device can be inserted into a desired location within the body of the patient. The mesh structure of the anchoring device can be used to help anchor or support the implantable medical device to surrounding tissue. Some known anchoring devices are used to provide temporary support to tissue during a healing process. For example, a mesh anchoring device can secure one portion of tissue to another portion of tissue.

In some known non-biodegradable anchoring devices, removal or explantation of the device can be difficult. For example, the mass of the device can result in an undesirable amount of fibrotic in-growth of surrounding tissue to the anchoring device, which can make it difficult to remove the anchoring device without damaging the surrounding tissue. In such a situation, the tissue in-growth can also result in an undesirable portion of the material of the anchoring device remaining in the patient's body after the treatment has been completed. Some known non-biodegradable anchoring devices can be too stiff or have an undesirable mass which can also result in the device being difficult to explant. Some known biodegradable anchoring devices may have insufficient strength for a particular use and/or may not provide the desired amount of support for a particular use. Some known biodegradable anchoring devices include a biodegradable polymer coating to help strengthen the anchoring device.

Thus, there is a need for an anchoring device that can be used to support tissue and/or to support an implantable medical device to tissue and that has reduced mass, and can be easily explanted from a patient's body, and which could elute an active pharmaceutical ingredient over time.

BRIEF SUMMARY OF THE INVENTION

In one aspect of the present invention is an anchorage device comprising a mesh substrate coupled to an implantable medical device, where the mesh substrate has a coating comprising a polymer and at least one active pharmaceutical ingredient ("API"). In one embodiment, the active pharmaceutical ingredient is selected from the group consisting of anesthetics, antibiotics, anti-inflammatory agents, procoagulant agents, fibrosis-inhibiting agents, anti-scarring agents, leukotriene inhibitors/antagonists, cell growth inhibitors and mixtures thereof. In another embodiment, the active pharmaceutical ingredient is an antibiotic. In another embodiment, the active pharmaceutical ingredient is selected from the group consisting of rifampin and minocycline and mixtures thereof.

In another embodiment, the polymer for the coating is selected from the group consisting of polylactic acid, polyglycolic acid, poly(L-lactide), poly(D,L-lactide) polyglycolic acid[polyglycolide], poly(L-lactide-co-D,L-lactide), poly(L-lactide-co-glycolide), poly(D, L-lactide-co-glycolide), poly(glycolide-co-trimethylene carbonate), poly(D,L-lactide-co-caprolactone), poly(glycolide-co-caprolactone), polyethylene oxide, polydioxanone, polypropylene fumarate, poly(ethyl glutamate-co-glutamic acid), poly(tert-butyloxy-carbonylmethyl glutamate), polycaprolactone, polycaprolactone co-butylacrylate, polyhydroxybutyrate, copolymers of polyhydroxybutyrate, poly(phosphazene), poly(phosphate ester), poly(amino acid), polydepsipeptides, maleic anhydride copolymers, polyiminocarbonates, poly[(97.5% dimethyl-trimethylene carbonate)-co-(2.5% trimethylene carbonate)], poly(orthoesters), tyrosine-derived polyarylates, tyrosine-derived polycarbonates, tyrosine-derived polyiminocarbonates, tyrosine-derived polyphosphonates, polyethylene oxide, polyethylene glycol, polyalkylene oxides, hydroxypropylmethylcellulose, polysaccharides such as hyaluronic acid, chitosan and regenerate cellulose. In another embodiment, the polymer is a polyarylate. In some embodiments, the polymer is a tyrosine-derived polyarylate. In other embodiments, the tyrosine-derived polyarylate is p(DTE co X % DT succinate), where X is about 10% to about 30%. In yet other embodiments, the tyrosine-derived polyarylate is p(DTE co X % DT succinate), where X ranges from about 26.5% to about 28.5%. In yet further embodiments, the tyrosine-derived polyarylate is p(DTE co X % DT succinate), where X is about 27.5%. In some embodiments, the polymer is P22-27.5DT. In other embodiments, the polymer is p22-27.5DT and the API is minocycline, rifampin, and mixtures thereof.

In another embodiment, the API is released from the coating over a time period ranging from about 1 h to about 168 h. In another embodiment, the API is released from the coating over a time period ranging from 1 h to 72 h. In another embodiment, the API is released from the coating over a time period ranging from 1 h to 24 h. In another embodiment, the polymer is a polyarylate and the API is an antibiotic. In another embodiment, the polymer is a tyrosine-derived polyarylate consisting of and the API is selected from the group consisting of rifampin and minocycline, and the API is eluted over a period of time ranging from about 1 h to about 24 h.

In another embodiment, the mesh covers only a portion of the implantable medical device. In another embodiment, the mesh is formed by knitting. In another embodiment, the mesh comprises pores ranging in size from about 1 mm to about 5 mm. In another embodiment, the mesh has a low areal density. In another embodiment, an amount of API in the coating ranging from between about 5% to about 30% by total weight of the coating. In another embodiment, the coating has a thickness ranging from about 5 μm to about 200 μm.

In another aspect of the present invention is a method of preventing, mitigating, or treating a bacterial infection comprising implanting the anchorage device comprising a mesh substrate coupled to an implantable medical device, where the mesh substrate has a coating comprising a polymer and at least one antibacterial or antimicrobial agent. In another embodiment, the active pharmaceutical ingredient is selected from the group consisting of rifampin and minocycline and mixtures thereof. In another embodiment, the API is released from the coating over a time period ranging from about 1 h to about 120 h.

In some embodiments, the polymer coating can be capable of releasing one or more drugs into surrounding bodily tissue to reduce or prevent surgery-related complications associated with the implantable medical device (such as to the "pocket" surrounding the device). For example, an anesthetic agent in the polymer coating can be eluted into the surrounding bodily tissue, bodily fluid, or systemic fluid, to attenuate pain experienced at the implantation site. In another example, replacing the anesthetic agent with an anti-inflammatory agent can reduce the swelling and inflammation associated implantation of the mesh substrate and/or the implantable medical device. In yet another example, an antimicrobial agent can be provided at a rate of drug release sufficient to prevent or reduce colonization of the mesh substrate, the implantable medical device and/or the surgical implantation site by bacteria, for example, for at least the period following surgery necessary for initial healing of the surgical incision.

In another aspect of the present invention is an anchorage device having temporally changing mechanical properties comprising a mesh substrate coupled to an implantable medical device, said mesh substrate having a polymer coating which (1) imparts a first stiffness at implantation, (2) has a second stiffness at a time between initial implantation and 3-months post-implantation, and (3) has a third stiffness at a time between 3-months and 24-months post-implantation. In some embodiments, the first stiffness is about 10 newtons. In other embodiments, the second stiffness is about 2 newtons. In other embodiments, the third stiffness is less than about 1 newton. In other embodiments, the anchorage device further comprises at least one active pharmaceutical ingredient within the polymer coating. In some embodiments, the active pharmaceutical ingredient is an antibiotic, preferably a mixture of rifampin and minocycline.

Without wishing to be bound by any particular theory, it is believed that by eluting an antimicrobial agent over time to an area surrounding or adjacent to a transdermal medical device, the incidence of microbial infections may be reduced, prevented, or mitigated, especially against those organisms described herein.

In another aspect of the present invention, devices and methods are described for use in supporting an implantable medical device, such as a cardiac defibrillator or a pacemaker, in a desired position at a treatment site within a body of a patient. In some embodiments, an anchorage device can include a mesh substrate that defines a pocket or envelope in which an implantable medical device can be at least partially disposed. In other embodiments, the mesh substrate can be secured to tissue to support the implantable medical device at the treatment site. In other embodiments, the mesh substrates of these embodiments have a smaller surface area, less tissue contact and therefore require less dissection to remove. In other embodiments, means of improving explantation include a device which is at least partially constructed of a mesh having very small or no pores at all, such that tissue will not grow into it, and that portion of the device will not require dissection of tissue to remove. In other embodiments, the implantable medical device can be configured to reduce the mass of the device such that it is not necessary to explant the device. In other embodiments, the means of reducing the mass of the device include using a mesh having a low areal density or a mesh with one or more apertures larger than the pore size of the mesh to reduce the mass of the substrate. In other embodiments, the entire device can be constructed of resorbable material. In other embodiments, a biodegradable polymer coating can be disposed on at least a portion of the mesh substrate. The polymer coating can include a drug that can be released at the treatment site.

In other embodiments, an anchorage device as described herein can be used to provide a physical barrier between various types of tissue or provide support and strength to a physical defect in soft tissue. In yet other embodiments, the anchorage devices described herein can be configured to reduce the amount of associated post-surgical complications that can occur with such implantable medical devices, such as, for example, post-implant infection, pain, excessive scar tissue formation and shrinkage of the prosthesis or mesh, excessive scar tissue formation, limited patient mobility, and/or chronic pain. In yet other embodiments, the size, shape, and/or mass of the anchorage device can be varied to reduce the amount of scar tissue formation and tissue in-growth. In yet further embodiments, an anchorage device can be configured with lighter weight meshes using smaller fibers, larger weaves, and/or larger pore sizes as well as meshes woven from both non-resorbable and resorbable materials.

In some embodiments, an anchorage device can include a mesh substrate configured to reduce the mass of the anchorage device such that it does not require explantation. In other embodiments, the mesh substrate can be formed with a mesh having a low areal density. In some embodiments, the mesh substrate can include one or more apertures to reduce the mass of the anchorage device. In some embodiments the entire device can be constructed of a resorbable material or mixtures of resorbable materials.

In other embodiments, the shape and/or size of the anchorage device can be configured to reduce the surface area of the anchorage device in contact with tissue thus, it is believed, requiring less tissue dissection for removal while maintaining a desired amount of support for an implantable medical device and/or to tissue to which the anchorage device is to be secured.

As described herein, an anchorage device can include a variety of different configurations that provide for the anchorage device to be removed or explanted from a patient's body with reduced damage to surrounding tissue and/or reducing the portion of the anchorage device that remains within the patient's body after treatment has been completed. For example, various configurations of an anchorage device can have reduced mass to reduce the need to explant the anchoring device. Other examples include anchoring devices constructed at least partially of mesh with very small pores or entirely without pores to reduce tissue in-growth and/or scar tissue formation in that portion of the device

BRIEF DESCRIPTION OF THE DRAWINGS

FIG. 5A is a front view of an anchorage device according to another embodiment and FIG. 5B is a front view of the anchorage device of FIG. 5A shown with a polymer coating.

FIGS. 8A, 8B and 8C are each a graph showing drug release versus time for three example procedures.

FIG. 10 is a graph showing the cumulative release of rifampin and ketoprofen.

FIG. 11 is a graph showing the cumulative release of rifampin and dexamethasone.

FIG. 12 is a graph showing the cumulative release of minocycline and rifampin.

FIG. 13 is a graph showing the cumulative release of minocycline and rifampin.

DETAILED DESCRIPTION

Figure 1:
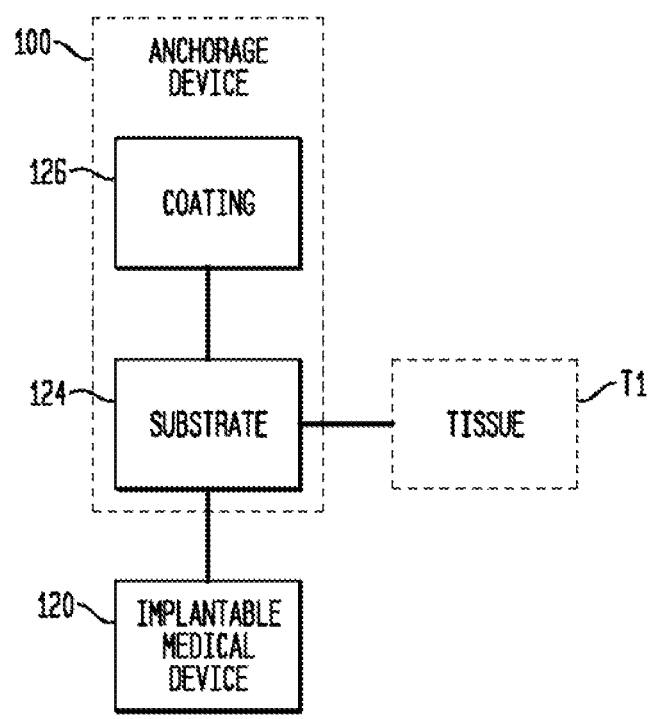
FIG. 1 is a schematic illustration of an anchorage device according to an embodiment.

Devices and methods are described herein for use, for example, in supporting or anchoring (collectively referred to herein as an "anchoring device" or "anchorage device") an implantable medical device to tissue within a body of a patient, and/or for supporting tissue within the patient's body. The devices may comprise one or more active pharmaceutical ingredients or a pharmaceutical composition or formulation comprising one or more APIs (collectively referred to herein as "APIs"). As described further herein, the APIs may be coated onto a surface of the anchoring device, may be present within a polymer matrix on a surface of the medical device, or may be embedded within a polymer matrix or other material comprising the anchoring device itself. The APIs may be released over time, either locally in an area adjacent to or surrounding the anchoring device, or systemically.

As used herein, the term "active pharmaceutical ingredient" or "API" is used to include all types of therapeutic agents, whether small molecules or large molecules such as proteins, nucleic acids, and other biological agents of interest. The APIs of the invention can be used alone or in combination. The APIs may be part of a formulation with other active or inactive ingredients.

As used herein, the term "implantable medical device" (hereinafter "IMD") refers to a medical device which is inserted into a body cavity and, as that term is used herein, also includes non-implantable medical devices. Non-limiting examples of medical devices are set forth herein. These include vascular devices such as grafts (e.g., abdominal aortic aneurysm grafts, etc.), stents, catheters (including arterial, intravenous, blood pressure, stent graft, etc.), valves (e.g., polymeric or carbon mechanical valves,), embolic protection filters (including distal protection devices), vena cava filters, aneurysm exclusion devices, artificial hearts, cardiac jackets, and heart assist devices (including left ventricle assist devices), implantable defibrillators, electro-stimulation devices and leads (including pacemakers, lead adapters and lead connectors), implanted medical device power supplies, peripheral cardiovascular devices" atrial septal defect closures, left atrial appendage filters, valve annuloplasty devices, mitral valve repair devices, vascular intervention devices, ventricular assist pumps, and vascular access devices (including parenteral feeding catheters, vascular access ports, central venous access catheters); surgical devices such as sutures of all types, anastomosis devices (including anastomotic closures), suture anchors, hemostatic barriers, screws, plates, clips, vascular implants, tissue scaffolds, cerebro-spinal fluid shunts, shunts for hydrocephalus, drainage tubes, catheters including thoracic cavity suction drainage catheters, abscess drainage catheters, biliary drainage products, and implantable pumps; orthopedic devices such as joint implants, acetabular cups, patellar buttons, bone repair/augmentation devices, spinal devices (e.g., vertebral disks and the like), bone pins, cartilage repair devices, and artificial tendons; dental devices such as dental implants and dental fracture repair devices; drug delivery devices such as drug delivery pumps, implanted drug infusion tubes, drug infusion catheters, and intravitreal drug delivery devices; ophthalmic devices such as scleral buckles and sponges, glaucoma drain shunts and intraocular lenses; urological devices such as penile devices (e.g., impotence implants), sphincter, urethral, prostate, and bladder devices (e.g., incontinence devices, benign prostate hyperplasia management devices, prostate cancer implants, etc.), urinary catheters including indwelling ("Foley") and non-indwelling urinary catheters, and renal devices; synthetic prostheses such as breast prostheses and artificial organs (e.g., pancreas, liver, lungs, heart, etc.); respiratory devices including lung catheters; neurological devices such as neurostimulators, neurological catheters, neurovascular balloon catheters, neuro-aneurysm treatment coils, and neuropatches, splints, ear wicks, ear drainage tubes, tympanostomy vent tubes, otological strips, laryngectomy tubes, esophageal tubes, esophageal stents, laryngeal stents, salivary bypass tubes, and tracheostomy tubes; oncological implants; and pain management implants.

Classes of suitable non-implantable devices can include dialysis devices and associated tubing, catheters, membranes, and grafts; autotransfusion devices; vascular and surgical devices including atherectomy catheters, angiographic catheters, intraaortic balloon pumps, intracardiac suction devices, blood pumps, blood oxygenator devices (including tubing and membranes), blood filters, blood temperature monitors, hemoperfusion units, plasmapheresis units, transition sheaths, dialators, intrauterine pressure devices, clot extraction catheters, percutaneous transluminal angioplasty catheters, electrophysiology catheters, breathing circuit connectors, stylets (vascular and non-vascular), coronary guide wires, peripheral guide wires; dialators (e.g., urinary, etc.); surgical instruments (e.g. scalpels and the like); endoscopic devices (such as endoscopic surgical tissue extractors, esophageal stethoscopes); and general medical and medically related devices including blood storage bags, umbilical tape, membranes, gloves, surgical drapes, wound dressings, wound management devices, needles, percutaneous closure devices, transducer protectors, pessary, uterine bleeding patches, PAP brushes, clamps (including bulldog clamps), cannulae, cell culture devices, materials for in vitro diagnostics, chromatographic support materials, infection control devices, colostomy bag attachment devices, birth control devices; disposable temperature probes; and pledgets.

As used herein, the term "mesh" refers to a mesh, pouch, bag, covering, shell, skin or receptacle comprised of a solid or semi-solid material. A mesh in accordance with the invention is any web or fabric with a construction of knitted, braided, woven or non-woven filaments or fibers that are interlocked in such a way to create a fabric or a fabric-like material that includes a matrix of filaments that define multiple pores.

As used herein, the term "biodegradable" refers to, for example, a material that can be at least partially broken down or degraded by a bodily fluid and discarded as waste from the body. Thus, "non-biodegradable" can refer to a material that cannot be broken down or degraded by a bodily fluid.

As used herein the term "resorbable" refers to, for example, a material that can be at least partially broken down or degraded by a bodily fluid and assimilated within the body. Thus, a "non-resorbable" material as used herein can refer to, for example, a material that cannot be broken down or degraded by bodily fluid.

In some embodiments, an anchorage device as described herein includes a mesh substrate that defines a pocket or envelope in which an implantable medical device can be at least partially disposed or otherwise coupled thereto for implantation at a treatment site within a patient's body. The mesh substrate can be secured to tissue to support the implantable medical device at the treatment site. In some embodiments, an anchorage device as described herein can be used to help inhibit or reduce bacterial growth, provide pain relief and/or inhibit scarring or fibrosis on or around the implantable medical device.

FIG. 1 is a schematic illustration of an anchorage device according to an embodiment. An anchorage device 100 includes a mesh substrate 124 that can be coupled to an implantable medical device 120 for implantation at a desired treatment site within a body of a patient. The anchorage device 100 can support and/or immobilize the implantable medical device 120 to surrounding tissue, such as a tissue portion T1, shown in FIG. 1. In some embodiments, the anchorage device 100 can be used alone (e.g., without an implantable medical device 120) to provide support for a tissue portion, such as, tissue portion T1. For example, the anchorage device 100 can be configured as a hernia mesh that is used to support the affected tissue(s) during healing.

The mesh substrate 124 (also referred to herein as "substrate") can define a pouch, pocket, envelope or other coupling portion configured to receive or couple thereto the implantable medical device 120. In some embodiments, the mesh substrate 124 can encase or surround at least a portion of the implantable medical device 120. As described above, the anchorage device 100 can be used, for example, to secure the implantable medical device 120 at a desired treatment site within a body of a patient, provide pain relief, inhibit scarring or fibrosis and/or inhibit bacterial growth.

The mesh substrate 124 can be formed with one or more sheets or portions of mesh material that can be secured to tissue within a body. The sheets of mesh material can be laser cut to produce the desired shape and size of the substrate 124. The mesh material of the substrate 124 can accommodate and/or promote tissue in-growth when implanted within a body, or inhibit tissue in-growth to facilitate explantation. In some embodiments, the substrate 124 includes a single sheet of mesh material that forms a pouch, pocket or envelope configured to receive at least a portion of the implantable medical device 120 therein. In some embodiments, the substrate 124 can include more than one sheet of mesh material sealed together by heat, by ultrasound or by any other method known to those of ordinary skill in the art.

In some embodiments, a portion or side of the substrate 124 can be left open to permit insertion of the implantable medical device 120 and to allow leads or other wires coupled to the implantable medical device 120 to extend out of the substrate 120. For example, a first sheet of mesh material can be ultrasonically sealed to a second sheet of mesh material along a portion of a perimeter of the sheets of mesh material.

In some embodiments, the substrate 124 may be formed with one or more biocompatible materials, which may be synthetic or naturally occurring. Non-limiting examples of biocompatible materials include polypropylene, polyester, polytetrafluoroethylene, polyamides, silicones, polysulfones, metals, alloys, titanium, stainless steel, shape memory metals (e.g. Nitinol), and/or combinations thereof. In other embodiments, the substrate 124 can be formed entirely, or at least in part, with a non-biodegradable material, such as, for example, a non-biodegradable polymer. In yet other embodiments, the substrate 124 can be formed entirely with a non-biodegradable mesh material. In alternative embodiments, the substrate 124 can be formed with a non-resorbable material or a material that is both non-biodegradable and non-resorbable. In some embodiments, the substrate may include one or more APIs which may be eluted over time.

The substrate 124 may be at least partially coated with one or more coatings 126. In some embodiments, the coating 126 is a comprised of one or more APIs or a pharmaceutical formulation comprising one or more APIs. In other embodiments, the coating 126 is comprised of a biodegradable and/or resorbable polymer. In yet other embodiments, the coating 126 is comprised of one or more APIs embedded within a biodegradable and/or resorbable polymer or copolymer matrix.

Examples of biodegradable and resorbable polymers that may be used in the coatings, either alone or in combination with one or more APIs, are described, for example, in U.S. Patent Pub. No. 2008/0132922 and U.S. Patent Pub. No. 2008/0128315, the disclosures of which are incorporated herein by reference in their entireties. Other biodegradable and/or resorbable polymer coatings that can be used, alone or in conjunction with one or more APIs, are described in copending applications U.S. Patent Application Ser. No. 61/509,843 and PCT/US11/49140, the disclosures of each are incorporated herein by reference in their entireties.

Other polymers which may be used in the coating compositions of the present invention include, but are not limited to, polylactic acid, polyglycolic acid and copolymers and mixtures thereof such as poly(L-lactide) (PLLA), poly(D, L-lactide) (PLA,)polyglycolic acid[polyglycolide (PGA)], poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), poly(D,L-lactide-co-caprolactone) (PLA/PCL) and poly(glycolide-co-caprolactone) (PGA/PCL); polyethylene oxide (PEO), polydioxanone (PDS), polypropylene fumarate, poly(ethyl glutamate-co-glutamic acid), poly(tert-butyloxy-carbonylmethyl glutamate), polycaprolactone (PCL), polycaprolactone co-butylacrylate, polyhydroxybutyrate (PHBT) and copolymers of polyhydroxybutyrate, poly(phosphazene), poly(phosphate ester), poly(amino acid), polydepsipeptides, maleic anhydride copolymers, polyiminocarbonates, poly[(97.5% dimethyl-trimethylene carbonate)-co-(2.5% trimethylene carbonate)], poly(orthoesters), tyrosine-derived polyarylates, tyrosine-derived polycarbonates, tyrosine-derived polyiminocarbonates, tyrosine-derived polyphosphonates, polyethylene oxide, polyethylene glycol, polyalkylene oxides, hydroxypropylmethylcellulose, polysaccharides such as hyaluronic acid, chitosan and regenerate cellulose, and proteins such as gelatin and collagen, and mixtures and copolymers thereof, among others as well as PEG derivatives or blends of any of the foregoing.

In some embodiments, biodegradable polymers of the invention have diphenol monomer units that are copolymerized with an appropriate chemical moiety to form a polyarylate, a polycarbonate, a polyiminocarbonate, a polyphosphonate or any other polymer.

The preferred biodegradable polymers are tyrosine-based polyarylates including those described in U.S. Pat. Nos. 4,980,449; 5,099,060; 5,216,115; 5,317,077; 5,587,507; 5,658,995; 5,670,602; 6,048,521; 6,120,491; 6,319,492; 6,475,477; 6,602,497; 6,852,308; 7,056,493; RE37,160E; and RE37,795E; as well as those described in U.S. Patent Application Publication Nos. 2002/0151668; 2003/0138488; 2003/0216307; 2004/0254334; 2005/0165203; and those described in PCT Publication Nos. WO99/52962; WO 01/49249; WO 01/49311; WO03/091337. These patents and publications also disclose other polymers containing tyrosine-derived diphenol monomer units or other diphenol monomer units, including polyarylates, polycarbonates, polyiminocarbonates, polythiocarbonates, polyphosphonates and polyethers. The foregoing patents and publications describe methods for making these polymers, some methods of which may be applicable to synthesizing other biodegradable polymers. Finally, the foregoing patents and publications also describe blends and copolymers with polyalkylene oxides, including polyethylene glycol (PEG). All such polymers are contemplated for use in the present invention.

As used herein, DTE is the diphenol monomer desaminotyrosyl-tyrosine ethyl ester; DTBn is the diphenol monomer desaminotyrosyl-tyrosine benzyl ester; DT is the corresponding free acid form, namely desaminotyrosyl-tyrosine. BTE is the diphenol monomer 4-hydroxy benzoic acid-tyrosyl ethyl ester; BT is the corresponding free acid form, namely 4-hydroxy benzoic acid-tyrosine.

P22 is a polyarylate copolymer produced by condensation of DTE with succinate. P22-10, P22-15, P22-20, P22-xx, etc., represents copolymers produced by condensation of (1) a mixture of DTE and DT using the indicated percentage of DT (i.e., 10, 15, 20 and xx % DT, etc.) with (2) succinate.

Additional preferred polyarylates are copolymers of desaminotyrosyl-tyrosine (DT) and an desaminotyrosyl-tyrosyl ester (DT ester), wherein the copolymer comprises from about 0.001% DT to about 80% DT and the ester moiety can be a branched or unbranched alkyl, alkylaryl, or alkylene ether group having up to 18 carbon atoms, any group of which can, optionally have a polyalkylene oxide therein. Similarly, another group of polyarylates are the same as the foregoing but the desaminotyrosyl moiety is replaced by a 4-hydroxybenzoyl moiety. Preferred DT or BT contents include those copolymers with from about 1% to about 30%, from about 5% to about 30% from about 10 to about 30% DT or BT. Preferred diacids (used informing the polyarylates) include succinate, glutarate and glycolic acid.

Additional biodegradable polymers useful for the present invention are the biodegradable, resorbable polyarylates and polycarbonates disclosed in U.S. provisional application Ser. No. 60/733,988, filed Nov. 3, 2005 and in its corresponding PCT Appln. No. PCT/US06/42944, filed Nov. 3, 2006. These polymers, include, but are not limited to, BTE glutarate, DTM glutarate, DT propylamide glutarate, DT glycineamide glutarate, BTE succinate, BTM succinate, BTE succinate PEG, BTM succinate PEG, DTM succinate PEG, DTM succinate, DT N-hydroxysuccinimide succinate, DT glucosamine succinate, DT glucosamine glutarate, DT PEG ester succinate, DT PEG amide succinate, DT PEG ester glutarate, DT PEG ester succinate, DTMB P(Desaminotyrsoyl tyrosine methylparaben ester-glutarate), and DTPP P(Desaminotyrsoyl tyrosine propylparaben ester-glutarate).

The most preferred polyarylates are the DTE-DT succinate family of polymers, e.g., the P22-xx family of polymers having from 0-50%, 5-50%, 5-40%, 1-30% or 10-30% DT, including but not limited to, about 1, 2, 5, 10, 15, 20, 25, 27.5, 30, 35, 40%, 45% and 50% DT. In some embodiments, the polymer is P22-27.5DT.

Additionally, the polyarylate polymers used in the present invention can have from 0.1-99.9% PEG diacid to promote the degradation process as described in U.S. provisional application Ser. No. 60/733,988. Blends of polyarylates or other biodegradable polymers with polyarylates are also preferred.

Methods of coating the mesh with a polymer and/or API are disclosed in U.S. Patent Publication No. 2008/0132922, the disclosure is hereby incorporated by reference herein. In some embodiments, the coating is sprayed onto the mesh. In other embodiments, the anchorage device is coated by dipping the mesh into the coating composition.

In some embodiments, the coatings have a thickness ranging from about 5 µm to about 200 µm. In other embodiments, the coatings have a thickness ranging from about 5 µm to about 20 µm. In yet other embodiments, the coatings have a thickness of about 10 µm.

The coating 126 may serve multiple purposes. In some embodiments, the coating 126 can provide stiffness or strength to the substrate 124. The stiffness may designed into the device or the coating on the device such that at certain times, the device will have a particular stiffness. In some embodiments, a coating is chosen for the device such that it at least temporarily stiffens the substrate. In other embodiments, a coating is chosen for the device such that it provides a stiffness that is at least about 1.1 times the stiffness of the substrate without the coating. In yet other embodiments, a coating is chosen for the device such that it provides a stiffness that is between about 1.1 to about 4.5 times the stiffness of the substrate without the coating. In yet further embodiments, a coating is chosen for the device such that it provides a stiffness that is between about 1.25 to about 2 times the stiffness of the substrate without the coating.

In other embodiments where the coating comprises at least one API, the coating may allow for a release of an API over time, such as to prevent, treat, or mitigate the incidence of bacterial infections during or after surgical implantation of the anchorage device 100. It is possible to tailor the stiffness of the substrate 124 and/or the amount and/or rate of drug release from the coating(s) 126 by altering the (1) number of coatings, (2) thickness of the coatings, and (3) components used in the coatings.

Anchorage devices 100 comprising APIs may be coated with single or multiple coating layers 126, depending on the amount of API to be delivered, the type of API (e.g. mode of action), synergy between APIs when two or more different APIs are present, and desired release rate. Each coating layer 126 may contain the same or different polymers, the same or different APIs, and the same or different amounts of either the polymer or API components. For example, a first coating layer may contain an API, while the second coating layer contains either no API or a lower concentration of API. As another example, a first coating layer may comprise a first API in a first polymer, while the second coating layer comprises a second, different API in a polymer that is either the same or different than the first polymer in the first coating layer.

Any API may be incorporated into coatings of the present invention. Doses of such APIs are known to those of ordinary skill in the art and the amounts of any single API to include in any coating can readily be surmised. Any pharmaceutically acceptable form of the APIs of the present invention can be employed in the present invention, e.g., the free base or a pharmaceutically acceptable salt or ester thereof. Pharmaceutically acceptable salts, for instance, include sulfate, lactate, acetate, stearate, hydrochloride, tartrate, maleate, citrate, phosphate and the like.

Examples of APIs suitable for use with the present invention include anesthetics, antibiotics (or "antimicrobials", the terms used interchangeably herein), anti-inflammatory agents, procoagulant agents, fibrosis-inhibiting agents, anti-scarring agents, leukotriene inhibitors/antagonists, cell growth inhibitors and the like.

Examples of non-steroidal anti-inflammatories include, but are not limited to, naproxen, ketoprofen, ibuprofen as well as diclofenac; celecoxib; sulindac; diflunisal; piroxicam; indomethacin; etodolac; meloxicam; r-flurbiprofen; mefenamic; nabumetone; tolmetin, and sodium salts of each of the foregoing; ketorolac bromethamine; ketorolac bromethamine trometamine; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, 1, and racemic isomers); and the methyl, ethyl, propyl, isopropyl, n-butyl, sec-butyl, t-butyl, esters of acetylsalicylic acid.

Examples of anesthetics include, but are not limited to, licodaine, bupivacaine, and mepivacaine. Further examples of analgesics, anesthetics and narcotics include, but are not limited to acetaminophen, clonidine, benzodiazepine, the benzodiazepine antagonist flumazenil, lidocaine, tramadol, carbamazepine, meperidine, zaleplon, trimipramine maleate, buprenorphine, nalbuphine, pentazocain, fentanyl, propoxyphene, hydromorphone, methadone, morphine, levorphanol, and hydrocodone. Local anesthetics have weak antibacterial properties and can play a dual role in the prevention of acute pain and infection.

Examples of antibacterial agents or antimicrobials include, but are not limited to, triclosan, chlorhexidine, rifampin, minocycline (or other tetracycline derivatives), vancomycin, gentamycine, cephalosporins and the like. Further antibacterial agents or antimicrobials include aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; cefamandole nafate; cefepime and its hydrochloride, sulfate, and phosphate salt; cefdinir and its sodium salt; ceftriaxone and its sodium salt; cefixime and its sodium salt; cefpodoxime proxetil; meropenem and its sodium salt; imipenem and its sodium salt; cilastatin and its sodium salt; azithromycin; clarithromycin; dirithromycin; erythromycin and hydrochloride, sulfate, or phosphate salts ethylsuccinate, and stearate forms thereof, clindamycin; clindamycin hydrochloride, sulfate, or phosphate salt; lincomycin and hydrochloride, sulfate, or phosphate salt thereof, tobramycin and its hydrochloride, sulfate, or phosphate salt; streptomycin and its hydrochloride, sulfate, or phosphate salt; vancomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; ticarcillin and its disodium salt; sulbactam and its sodium salt; moxifloxacin; ciprofloxacin; ofloxacin; levofloxacins; norfloxacin; gatifloxacin; trovafloxacin mesylate; alatrofloxacin mesylate; trimethoprim; sulfamethoxazole; demeclocycline and its hydrochloride, sulfate, or phosphate salt; doxycycline and its hydrochloride, sulfate, or phosphate salt; minocycline and its hydrochloride, sulfate, or phosphate salt; tetracycline and its hydrochloride, sulfate, or phosphate salt; oxytetracycline and its hydrochloride, sulfate, or phosphate salt; chlortetracycline and its hydrochloride, sulfate, or phosphate salt; metronidazole; dapsone; atovaquone; rifabutin; linezolide; polymyxin B and its hydrochloride, sulfate, or phosphate salt; sulfacetamide and its sodium salt; and clarithromycin. In preferred embodiments the coatings contain rifampin and another antimicrobial agent, preferably that agent is a tetracycline derivative. In another preferred embodiment, the coatings contains a cephalosporin and another antimicrobial agent. Preferred combinations include rifampin and minocycline, rifampin and gentamycin, and rifampin and minocycline.

When a mixture of two antibiotics are used, they generally present in a ratio ranging from about 10:1 to about 1:10. In some embodiments, a mixture of rifampin and minocycline are used. In those embodiments, a ratio of rifampin to minocycline ranges from about 5:2 to about 2:5. In other embodiments, the ratio of rifampin to minocycline is about 1:1.

Examples of antifungals include amphotericin B; pyrimethamine; flucytosine; caspofungin acetate; fluconazole; griseofulvin; terbinafin and its hydrochloride, sulfate, or phosphate salt; ketoconazole; micronazole; clotrimazole; econazole; ciclopirox; naftifine; and itraconazole.

Other APIs that can be incorporated into the coatings on the mesh pouches of the invention include, but are not limited to, keflex, acyclovir, cephradine, malphalen, procaine, ephedrine, adriamycin, daunomycin, plumbagin, atropine, quinine, digoxin, quinidine, biologically active peptides, cephradine, cephalothin, cis-hydroxy-L-proline, melphalan, penicillin V, aspirin, nicotinic acid, chemodeoxycholic acid, chlorambucil, paclitaxel, sirolimus, cyclosporins, 5-fluorouracil and the like.

Additional, APIs include those that act as angiogenensis inhibitors or inhibit cell growth such as epidermal growth factor, PDGF, VEGF, FGF (fibroblast growth factor) and the like. These APIs include anti-growth factor antibodies (neutrophilin-1), growth factor receptor-specific inhibitors such as endostatin and thalidomide. Examples of useful proteins include cell growth inhibitors such as epidermal growth factor.

Examples of anti-inflammatory compound include, but are not limited to, anecortive acetate; tetrahydrocortisol, 4,9(11)-pregnadien-17α,21-diol-3,20-dione and its -21-acetate salt; 111-epicortisol; 17α-hydroxyprogesterone; tetrahydrocortexolone; cortisona; cortisone acetate; hydrocortisone; hydrocortisone acetate; fludrocortisone; fludrocortisone acetate; fludrocortisone phosphate; prednisone; prednisolone; prednisolone sodium phosphate; methylprednisolone; methylprednisolone acetate; methylprednisolone, sodium succinate; triamcinolone; triamcinolone-16,21-diacetate; triamcinolone acetonide and its -21-acetate, -21-disodium phosphate, and -21-hemisuccinate forms; triamcinolone benetonide; triamcinolone hexacetonide; fluocinolone and fluocinolone acetate; dexamethasone and its -21-acetate, -21-(3,3-dimethylbutyrate), -21-phosphate disodium salt, -21-diethylaminoacetate, -21-isonicotinate, -21-dipropionate, and -21-palmitate forms; betamethasone and its -21-acetate, -21-adamantoate, -17-benzoate, -17,21-dipropionate, -17-valerate, and -21-phosphate disodium salts; beclomethasone; beclomethasone dipropionate; diflorasone; diflorasone diacetate; mometasone furoate; and acetazolamide.

Examples of leukotriene inhibitors/antagonists include, but are not limited to, leukotriene receptor antagonists such as acitazanolast, iralukast, montelukast, pranlukast, verlukast, zafirlukast, and zileuton.

Another useful drug that can be incorporated into the coatings of the invention is sodium 2-mercaptoethane sulfonate ("MESNA"). MESNA has been shown to diminish myofibroblast formation in animal studies of capsular contracture with breast implants [Ajmal et al. (2003) *Plast. Reconstr. Surg.* 112:1455-1461] and may thus act as an anti-fibrosis agent.

Procoagulants include, but are not limited to, zeolites, thrombin, and coagulation factor concentrates.

In some embodiments, the amount of API included in the coating ranges between about 0.3 to about 2.8 micrograms/cm2. In other embodiments, the amount of API included in the coating ranges between about 0.6 to about 1.4 micrograms/cm2. In yet other embodiments, the amount of API included in the coating ranges between about 0.85 to about 1.20 micrograms/cm2. In yet further embodiments, the amount of API included in the coating ranges between about 0.90 to about 1.10 micrograms/cm2.

In other embodiments, the amount of each of rifampin and minocyclin included in the coating ranges between about 0.6 to about 1.4 micrograms/cm2. In yet other embodiments, the amount of each of rifampin and minocyclin included in the coating ranges between about 0.85 to about 1.20 micrograms/cm2. In yet further embodiments, the amount of each of rifampin and minocyclin included in the coating ranges between about 0.90 to about 1.10 micrograms/cm2.

In general, the coatings 126 are designed to release one or more APIs over time. In some embodiments, the APIs are eluted over time in an area surrounding or adjacent to the anchorage device 100 (such as, for example, within the device "pocket" or within 3 inches in all dimensions). In some embodiments, the API may be eluted for up to 30 days (see, e.g., FIGS. 10, 11, and 13). In some embodiments, between about 40% and about 100% of the APIs are release over a period of at least about 30 hours. In other embodiments, 60% and about 100% of the APIs are release over a period of at least about 30 hours. In other embodiments, between about 65% and about 100% of the APIs are release over a period of at least about 36 hours. In other embodiments, 80% and about 100% of the APIs are release over a period of at least about 36 hours. In other embodiments, between about 60% and about 100% of the APIs are release over a period of at least about 48 hours. In other embodiments, 80% and about 100% of the APIs are release over a period of at least about 48 hours. In other embodiments, between about 60% and about 100% of the APIs are release over a period of at least about 60 hours. In other embodiments, 80% and about 100% of the APIs are release over a period of at least about 60 hours.

In yet further embodiments, no more than 60% of the APIs are released within 24 hours. In even further embodiments, no more than 90% of the APIs are released after 60 hours. In one embodiment, no more than 50% of the APIs are released within 12 hours; between about 40% and about 90% are released between 12 and 24 hours; between about 60% and about 100% are released between 24 and 36 hours; between about 65% and about 100% are released between 36 and 48 hours; and between about 70% and about 100% are released between 48 and 60 hours.

In some embodiments, the coated devices may be used to prevent, treat or mitigate bacterial colonization or infections. In some embodiments, the coating comprises an antibacterial agent(s), such that the antimicrobial agent(s) may be eluted over time. In other embodiments, the coating comprises minocycline, rifampin, or a mixture of minocycline and rifampin. In other embodiments, the antibacterial agent is eluted over a period of at least 24 hours. In yet further embodiments, the cumulative release of antibacterial agent is at least about 30% over 24 hours. In yet further embodiments, the cumulative release of antimicrobial agent is at least about 40% over 24 hours. In yet other embodiments, the cumulative release of antimicrobial agent is at least about 50% over 24 hours. In yet further embodiments, at least about 80% of the antimicrobial agent is released after 3 days. Of course, these release rates may be varied by choosing different polymer coating compositions as recognized by those of skill in the art.

In one embodiment, an anchorage device 100 can be configured to be used in the implantation of an implantable medical device 120 that is a cardiovascular implantable electronic device CIED. In such an embodiment, the anchorage device 100 can include a polymer coating 126 that includes a pharmacokinetic profile of antibiotic configured to be released into the surrounding tissue adjacent to the implanted CIED to reduce or prevent CIED infection. Such a pharmacokinetic profile of antibiotic release from the polymer coating 126 can define a spatial and temporal distribution of the antibiotic with respect to the implanted CIED, which can determine the clinical efficacy and safety of the implantable CIED. In some embodiments, the pharmacokinetic profile of antibiotic release adjacent to the implanted CIED can achieve an optimal efficacy and safety for CIED infection prophylaxis. The pharmacokinetic profile of in vivo antibiotic release from an implanted CIED designed to prevent or reduce CIED infections can be characterized by several features that can include, for example: (1) less than 75% of the antibiotics can be released by the polymer coating in the first 24 hours after implantation of the CIED; (2) more than 80% of the antibiotics can be released by the polymer coating in the first 48 hours after implantation of the CIED; (3) more than 95% of the antibiotics can be released from the polymer coating in the first seven days after implantation of the CIED; (4) no antibiotic is detectable in the systemic circulation at 1 hour, 24 hours, and 72 hours after implantation of the CIED, with an assay that has a sensitivity of at least 500 ng/ml; or (5) the antibiotic can achieve a level equal or exceeding the Minimum Inhibitory Concentration ("MIC") of the antibiotic for methicillin-resistant *Staphylococcus aureus* on both sides of the CIED for at least 48 hours after implantation of the CIED. In these embodiments, any antibiotic or antimicrobial compound(s) may be used. In particularly preferred embodiments, the antibiotic or antimicrobial compound is selected from the group consisting of rifampin, minocycline, and mixtures thereof.

The coatings of the present invention may comprise between about 1% and about 50% of one or more APIs by total weight of the coating. In some embodiments, the coatings of the present invention may comprise between about 5% and about 30% of one or more APIs by total weight of the coating. In other embodiments, the coatings of the present invention may comprise between about 6% and about 25% of one or more APIs by total weight of the coating.

In some embodiments, the API is eluted locally, such as within 3 inches of the IMD or CIED in all directions or dimensions, preferably within 2.5 inches in all directions; more preferably within 2 inches in all directions.

In some embodiments, the profile of the anchorage device 100 can have temporally changing mechanical properties that are deliberately synchronized to distinct requirements during different phases of the implantation and maturation of the anchorage device configured to be implanted with a CIED and configured to prevent and/or reduce CIED infections. For example, the clinical performance of the anchorage device implanted in a CIED generator pocket to prevent CIED infection can be substantially improved if the chemical composition of the polymer coating 126 of the anchorage device 100 used to support the CIED can be defined to allow the mechanical properties of the anchorage device to change in a manner that is synchronized to the clinical events that occur in the time period from implantation to the completion of scar formation in the pocket. Some key qualitative features of this temporally changing profile can include, for example: (1) At implantation, the anchorage device should be maximally stiffened by the polymer to facilitate insertion of the device into the generator pocket that is created from a potential space between the subcutaneous tissue and the anterior surface of the pectoralis muscle or between posterior aspect of the pectoralis muscle and adjacent structure. (2) After implantation is complete, the majority of wound healing occurs during the next 3 months. During this period, some degree of residual stiffness is optimal because it prevents the edges of the anchorage device from being maneuvered from the intended implantation site into the healing wound. (3) During the final phase of pocket maturation, which occurs from 3 months to 24 months after implantation, scar tissue forms around the anchorage device and the determines its final orientation. During this phase, significantly reduced flexibility is optimal because it will permit the anchorage device to assume the final shape of the pocket, minimizing the chance that a stiff edge of the anchorage device will protrude into the subcutaneous tissue and precipitate an erosion. Such devices may further comprise and antibiotic, preferably a mixture of rifampin and minocycline.

The corresponding key quantitative features of this temporally changing mechanical profile can include, for example: (1) Early (implantation): stiffness=10 newtons; (2) Initial 3 months after implantation: stiffness=2; and (3) 3-24 months after implantation: stiffness=<1.

The anchorage device 100 can have a variety of different configurations, shapes and sizes that can provide the functionality of supporting and immobilizing the implantable medical device 120 at a treatment site within a patient's body, while also improving the removability of the anchorage device 100 after the treatment has been completed. For example, in use, the implantable medical device 120 can be disposed within the pocket defined by the mesh substrate 124 and the anchorage device 100 can be implanted and secured to tissue at a desired treatment site within a body of a patient. As described above, during implantation, scar tissue can form at the treatment site and/or tissue can become ingrown within the mesh substrate 124. After the treatment is completed, the implantable medical device 120 can be removed from the patient leaving the anchorage device 100 implanted. To remove the anchorage device 100, tissue that is ingrown within the mesh substrate 124 can be cut or otherwise detached from the mesh substrate 124. In some embodiments, a portion of the anchorage device 100 may not be removable from the tissue and will remain implanted within the patient. In embodiments where the anchorage device 100 is made from a biodegradable or resorbable polymer, the remaining anchorage device be broken down over time as known to those of ordinary skill in the art.

The anchorage device 100 can be configured to reduce the amount of tissue in-growth and/or scar tissue and/or reduce the overall mass of the anchorage device 100 such that the portion of the anchorage device 100 that remains implanted can be more easily explanted if desired or left in the body permanently For example, in some embodiments, it may be desirable to limit an amount of the anchorage device 100 left implanted within the patient's body to a mass of 100 mg.

To reduce the mass of the anchorage device 100 during the implantation period, in some embodiments, the anchorage device 100 can include a substrate 124 that has a portion or portions that are formed with a non-biodegradable material and one or more portions that are formed with a biodegradable material. In such an embodiment, the anchorage device 100 can be implanted, for example, with the non-biodegradable portion(s) disposed in contact with the tissue. In this position, the biodegradable portion(s) can degrade during implantation providing easy access for removal of the implantable medical device 120.

Alternatively, the biodegradable portion(s) of the substrate 124 can be disposed in contact with the tissue. As the biodegradable portion(s) degrades, the substrate 124 will reduce in mass and reduce the surface areas of the substrate 124 that is in contact with the surrounding tissue. The remaining non-biodegradable portion(s) will have mass small enough so as not to require explantation. The non-biodegradable portion(s) of the substrate 124 can be removed from a patient's body when the treatment is completed by cutting any in-grown tissue. In some embodiments, substantially all of the non-biodegradable portion(s) of the anchorage device 100 can be removed from the patient's body. In some embodiments, due to reduced mass a portion or portions of the non-biodegradable portion(s) of the substrate may remain implanted within the patient's body.

In another embodiment to reduce the overall mass of the anchorage device 100, the substrate 124 can be formed with a mesh material having a relatively low areal density (e.g., surface density). For example, the substrate 124 can be formed with a mesh material that includes pores that are larger than the pores of other known mesh anchorage devices. The larger pore size can reduce the overall mass of the anchorage device, and therefore, in some cases can eliminate the need for explantation. In some embodiments, the pores range in size between about 5 mm to about 10 mm. In other embodiments, the pores range are greater than about 1 mm in size.

In some embodiments, the substrate 124 can include one or more apertures in addition to the pores of the mesh material that can reduce the overall mass of the anchorage device 100. In some such embodiments, the one or more apertures can be covered with a biodegradable and/or resorbable film or coating. For example, the film can be a biodegradable and/or resorbable polymer. In some embodiments, the film can include an API that can be eluted into the patient's body as the film degrades in similar manner as described above for the polymer coating 126. After the film has degraded, the remaining portion of the mesh substrate 124 can have a reduced mass, and therefore, in some cases can eliminate the need for explantation.

In some embodiments, the mass of the anchorage device 100 can be reduced by including a substrate 124 that defines a pocket or envelope that covers only a portion of the implantable medical device 120. In such an embodiment, the surface area and mass of the substrate 124 can be reduced, and thus, tissue in-growth and scar tissue formation can be reduced and less tissue dissection is required to remove the anchorage device.

In some embodiments, the construction of the anchorage device 100 can be configured to aid in the removal of the anchorage device 100. For example, in some embodiments, the substrate 124 can be formed with a mesh material that is knitted such that the substrate 124 can be removed from the patient's body by unraveling a filament or filaments of the mesh substrate 124. In such an embodiment, the substrate 124 can be knitted into a configuration which allows it to be unraveled into an individual filament or multiple filaments. As the substrate 124 is unraveled, only an individual filament of material having a small diameter is being pulled or detached from the tissue, and therefore, can result in a reduction or elimination in possible damage to the tissue.

In some embodiments, the substrate 124 can be formed with a flexible shape-memory material that allows the anchorage device 100 to be moved between a biased collapsed configuration when not in use to an expanded configuration when the implantable medical device 120 is disposed within a pocket or pouch of the anchorage device 100. In such an embodiment, the anchorage device 100 and implantable medical device 120 can be implanted within a patient and when the treatment is completed, the implantable medical device 120 can be removed from the anchorage device 100. After the implantable medical device 120 is removed from the anchorage device 100, the anchorage device 100 can assume its biased collapsed configuration. As the anchorage device 100 moves to its collapsed configuration, a portion or portions of the substrate 124 can pull away and detach from the surrounding tissue to aid in the removal of the anchorage device 100. In some embodiments, the shape memory metal is Nitinol.

Figure 2A:
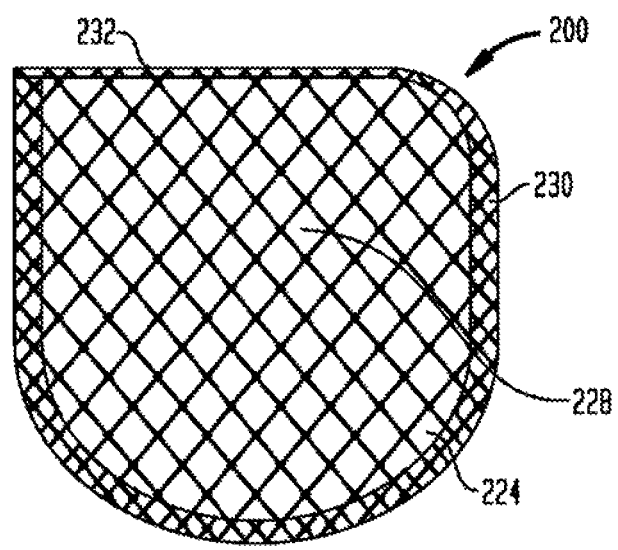
FIG. 2A is a front view of an anchorage device according to an embodiment.

FIG. 2A illustrates an example embodiment of an anchorage device according to an embodiment. As shown in FIG. 2A, an anchorage device 200 includes a mesh substrate 224 that can be formed with one or more sheets of mesh material as described above for substrate 124. The anchorage device 200 can also include a biodegradable polymer coating (not shown in FIG. 2) disposed on at least a portion of the mesh substrate 224 and the polymer coating can include a drug to be released into the body of the patient as the polymer coating degrades during implantation.

The mesh substrate 224 includes two sheets of mesh material that are sealed along a perimeter 230 of the mesh substrate 224 to define a pocket (not shown) that can receive an implantable medical device (not shown) therein. A portion of a side 232 along the perimeter 230 is not sealed such that an opening is defined through which the implantable medical device can be inserted into the pocket. The mesh substrate 224 can be formed with, for example, a non-biodegradable material or a non-resorbable material. In alternative embodiments, the mesh substrate 224 can be formed from a single sheet of mesh material such as by knitting as described above for substrate 124.

Figure 2B:
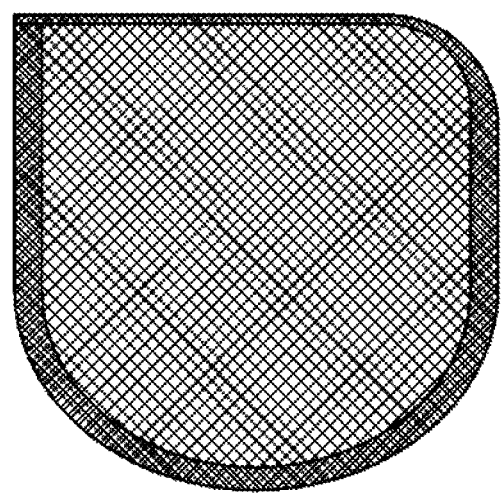
FIG. 2B is front view of an example prior art anchorage device.

In this embodiment, the mesh substrate 224 defines pores 228 that are larger than the pores of the other known mesh devices, for example, as shown in FIG. 2B, which illustrates an example of a prior art mesh anchorage device. The larger pores 228 can provide the mesh substrate 224 with a relatively low areal density that can help reduce scar formation and tissue in-growth. In some embodiments, the pores have a dimension in at least one direction of greater than about 1 mm. In other embodiments, the pores have a dimension in at least one direction of greater than about 1.2 mm. In yet other embodiments, the pores have a dimension in at least one direction of greater than about 1.4 mm. In yet further embodiments, the pores have a dimension in at least one direction of greater than about 1.6 mm.

Figure 3:
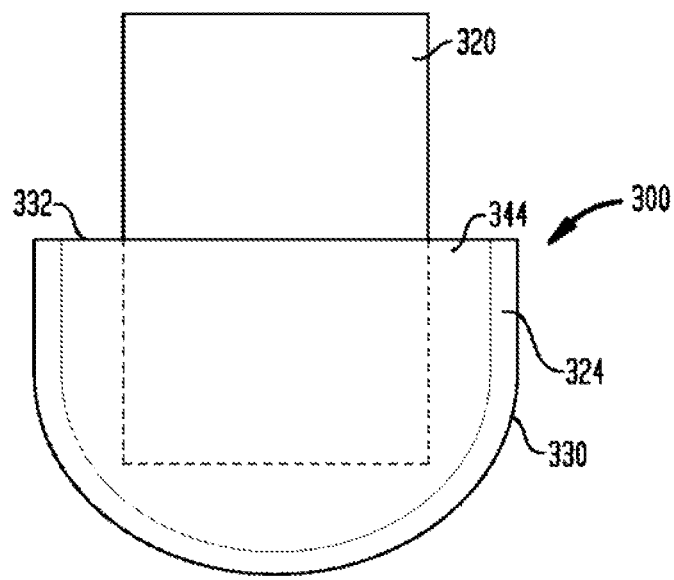
FIG. 3 is a front view of an anchorage device according to another embodiment shown with a schematic illustration of an implantable medical device coupled to the anchorage device.

FIG. 3 illustrates an embodiment of an anchorage device according to another embodiment. An anchorage device 300 includes a mesh substrate 324 that can be formed with two sheets of mesh material that are sealed along a perimeter 330 as described above for mesh substrate 224. The mesh substrate 324 can be formed with, for example, a non-biodegradable material or a non-resorbable material and includes pores (not shown) that can be sized similar to or the same as described above for substrate 224 or another pore size as used in known surgical mesh material, such as, for example, a pore size as shown in the prior art anchorage device of FIG. 2B.

In this embodiment, the mesh substrate 324 defines a pocket 344 that receives only a portion of an implantable medical device 320 therein such that a portion of the implantable medical device 320 extends outside of the pocket 344, as shown in FIG. 3. A portion of a side 332 along the perimeter 330 defines an opening through which the implantable medical device 320 can be inserted into the pocket 344. The reduced size of the mesh substrate 324 reduces the surface area of the anchorage device 300 that is in contact with tissue at the treatment site, while maintaining sufficient strength to support the implantable medical device 320 during implantation. It is also believed that the mesh substrate anchors the device and prevents migration, i.e. movement outside the implantation pocket and the pocket area (which is about twice the size of the implanted device). In some embodiments, the pocket is defined as the area about 1 inch around the device in all dimensions.

As with the previous embodiments, the anchorage device 300 can also include a biodegradable polymer coating (not shown in FIG. 3) disposed on at least a portion of the mesh substrate 324 and the polymer coating can include a drug to be released into the body of the patient as the polymer coating degrades during implantation.

Figure 4A:
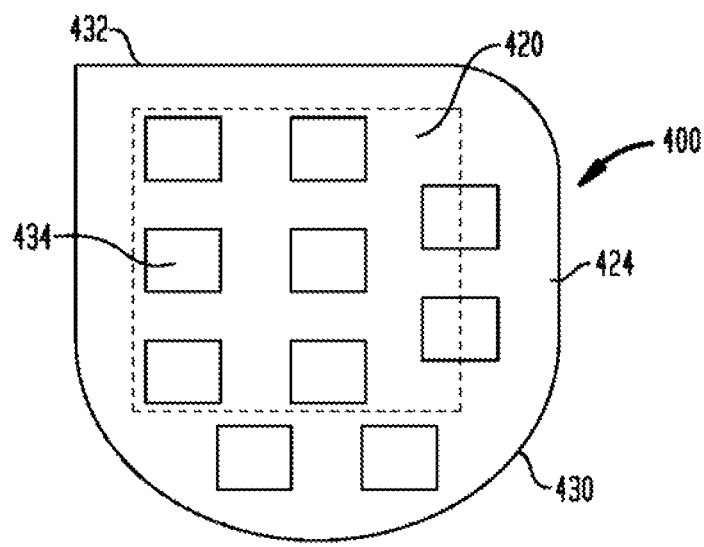
FIGS. 4A and 4B are each a front view of an anchorage device according to another embodiment.

FIG. 4A illustrates another embodiment of an anchorage device that has a reduced mass. An anchorage device 400 includes a mesh substrate 424 that can be formed with one or more sheets of mesh material that can be sealed along a portion of a perimeter 430 as described above for mesh substrates 224 and 324. In alternative embodiments, the mesh substrate 424 can be formed from a single sheet of mesh material such as, for example, by knitting. The mesh substrate 424 also defines a pocket (not shown) that can receive an implantable medical device 420 therein. A portion of a side 432 along the perimeter 430 is not sealed such that an opening is defined through which the implantable medical device 420 can be inserted into the pocket. The mesh substrate 424 can be formed with, for example, a non-biodegradable material or a non-resorbable material and includes pores (not shown) that can be sized similar to or the same as described above for previous embodiments.

In this embodiment, the mesh substrate 424 also defines multiple apertures 434 that are larger than the pore size of the mesh material of the mesh substrate 424. The multiple apertures 434 can reduce the mass of the anchorage device 400 and the surface area of the mesh substrate 424 where tissue in-growth can occur. For example, the size of the apertures 434 can be large enough such that tissue may not be able to bridge the apertures The low mass of the anchorage device 400 can in some cases allow the anchorage device 400 to be left implanted within the body of the patient after the treatment has been completed.

Although the apertures 434 are shown substantially square, it should be understood that the apertures 434 can be a variety of different shapes and sizes. For example the apertures 434 can be round, square, rectangular, oblong, diamond shaped, and/or triangular. The number of apertures 434 can also vary. For example, in some embodiments, only one aperture 434 may be included. In some embodiments, the apertures 434 can be formed on both sheets of the mesh material that form the substrate 424. In some embodiments, the apertures 434 can be formed on only one sheet of the mesh material (e.g., one side of the pocket) that forms the substrate 424.

Figure 4B:
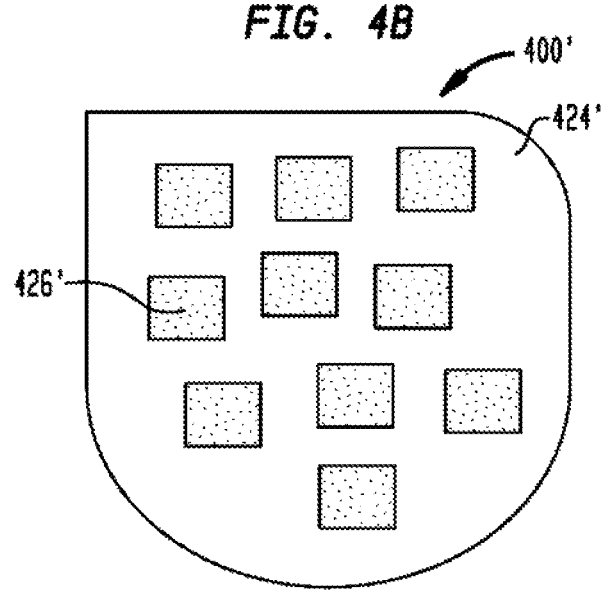

In alternative embodiments, and for applications other than with CIEDs where there needs to be electrical conduction between the CIED and the surrounding tissue, the apertures 434 can also be covered or filled with a biodegradable and/or resorbable polymer film or coating, as shown in FIG. 4B. In this variation, an anchorage device 400' includes a substrate 424' that includes multiple apertures that are covered with a biodegradable and/or resorbable polymer coating 426'. The coating 426' can optionally include a drug as described above for polymer coating 126 that can be released into the body of the patient as the coating 426' degrades or resorbs into the body.

As with previous embodiments, the anchorage device 400 and/or the anchorage device 400' can also include a biodegradable polymer coating (not shown in FIG. 4A or 4B disposed on at least a portion of the mesh substrate 424 or 424' and the polymer coating can include a drug to be released into the body of the patient as the polymer coating degrades during implantation.

Figure 5A:
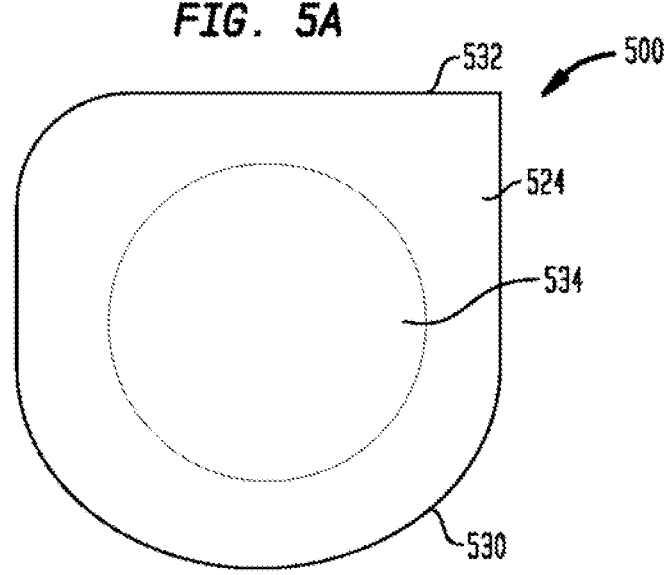

FIG. 5A illustrates another embodiment of an anchorage device that includes apertures to reduce the surface area and mass of the anchorage device. An anchorage device 500 includes a mesh substrate 524 that can be formed with one or more sheets of mesh material that can be sealed along a portion of a perimeter 530 as described above for mesh substrates 224, 324 and 424. In alternative embodiments, the mesh substrate 524 can be formed from a single sheet of mesh material such as by knitting. The mesh substrate 524 also defines a pocket (not shown) that can receive an implantable medical device (not shown) therein. A portion of a side 532 along the perimeter 530 defines an opening through which the implantable medical device can be inserted into the pocket. The mesh substrate 524 can be formed with, for example, a non-biodegradable material or a non-resorbable material and includes pores (not shown) that can be sized similar to or the same as described above for previous embodiments.

In this embodiment, the mesh substrate 524 also defines an aperture 534 on both sides of the pocket (e.g., on both sheets of mesh material used to form the substrate 524) forming a substantially toroidal or donut shape. The size of the apertures can be configured such that the mesh substrate 524 can prevent an implantable medical device disposed therein from slipping out. As with the previous embodiment, the apertures 534 can be covered with a biodegradable and/or resorbable polymer coating 526, as shown in FIG. 5B. The coating 526 can optionally include a drug that can be released into the body as the coating 526 degrades or resorbs into the body.

During implantation, the biodegradable coating 526 can eventually degrade and/or resorb into the body of the patient, leaving the anchorage device 500 with a frame of tissue around it (e.g., through tissue in-growth) that holds it in place. The implantable medical device can be removed from the body by pulling the implantable medical device through the aperture 534.

As with the previous embodiment, the apertures 534 can be a variety of different shapes and sizes. For example the apertures 534 can be round, square, rectangular, oblong, diamond shaped, or triangular. The number of apertures 534 can also vary. For example, in some embodiments, an aperture 534 may be included on only one side of the pocket of the substrate 524 (e.g., on one sheet of the mesh material used to form the mesh substrate 524). Also as with previous embodiments, the anchorage device 500 can include a biodegradable polymer coating (not shown in FIG. 5A or 5B) disposed on at least a portion of the mesh substrate 524 and the polymer coating can include a drug to be released into the body of the patient as the polymer coating degrades during implantation.

Figure 6A:
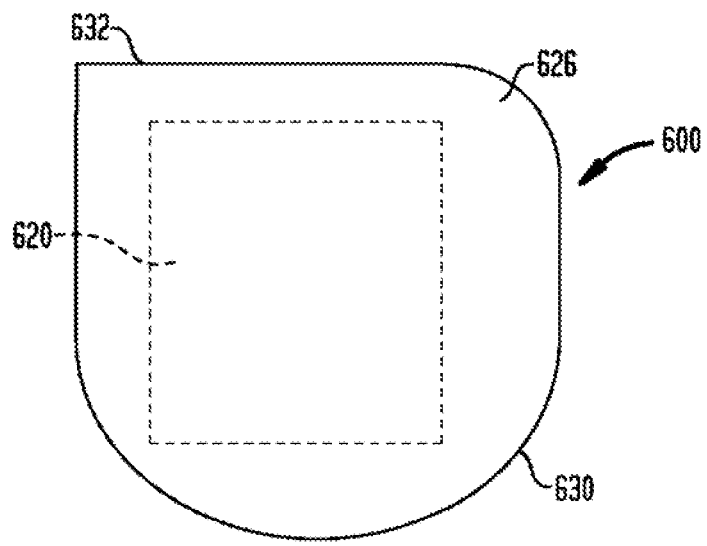
FIG. 6A is a front view of an anchorage device according to another embodiment and FIG. 6B is a side view of the anchorage device of FIG. 6A.
Figure 6B:
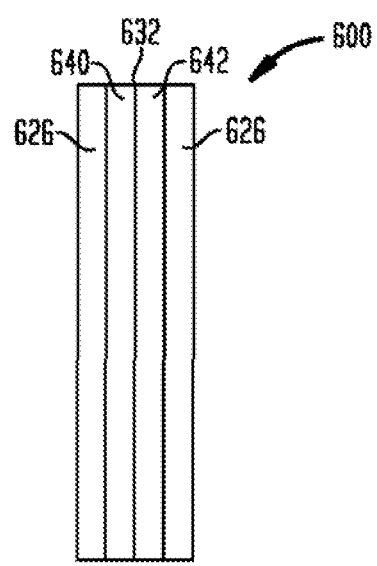

FIGS. 6A and 6B illustrate another embodiment of an anchorage device. An anchorage device 600 includes a mesh substrate 624 formed with a first sheet 640 of mesh material and a second sheet 642 of mesh material sealed along a portion of a perimeter 630 of the mesh substrate 624. The first sheet 640 and the second sheet 642 define a pocket (not shown) that can receive an implantable medical device 620 therein, and a portion of a side 632 along the perimeter 630 can define an opening through which the implantable medical device 620 can be inserted into the pocket.

In this embodiment, the first sheet 640 of the mesh substrate 624 can be formed with a non-biodegradable material or a non-resorbable material and includes pores (not shown) that can be sized similar to or the same as described above for previous embodiments. The second sheet 642 can be formed with a biodegradable material or a resorbable material and includes pores (not shown) that can be sized similar to or the same as described above for previous embodiments.

In this embodiment, other than for CIED applications where there needs to be electrical conduction between the CIED and the surrounding tissue, the mesh substrate 624 can optionally be substantially covered with a biodegradable and/or resorbable polymer coating 626. The polymer coating 626 can include a drug to be released into the body of the patient as the polymer coating 626 degrades during implantation as previously described for other embodiments.

In this embodiment, in one example implantation, the anchorage device 600 can be implanted within a patient's body with the biodegradable first sheet 640 of the substrate 624 contacting the surrounding tissue. The coating 626 will degrade or resorb, and the first sheet 640 will also degrade or resorb during implantation. Thus, the mass and surface area of the substrate 624 will be reduced during implantation. The second sheet 642 can be explanted from the body by cutting the tissue that has in-grown on the second sheet 642. Because the second sheet 642 is disposed facing away from the tissue, access to cut the ingrown tissue can be improved. Alternatively, in a second example implantation, the non-biodegradable second sheet 642 can be disposed facing the tissue. In this position, the biodegradable or resorbable first sheet 640 can degrade and/or resorb providing easy access for removal of the implantable medical device 620. Some or all of the second sheet 642 can be removed by cutting the surrounding ingrown tissue. Alternately, the first sheet 640 can be constructed of a non-resorbable material having very small or no pores, such that tissue in growth is reduced and explantation is facilitated.

Figure 7A:
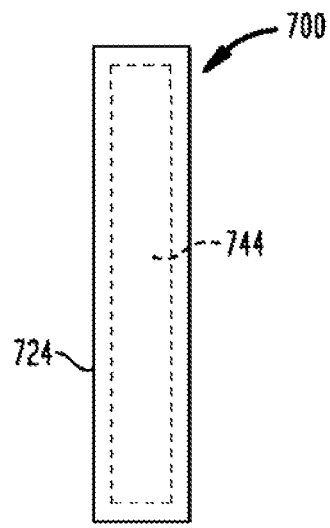
FIG. 7A is a schematic side view of an anchorage device according to another embodiment and shown in a first configuration and FIG. 7B is a schematic side view of the anchorage device of FIG. 7A shown with in a second configuration.
Figure 7B:
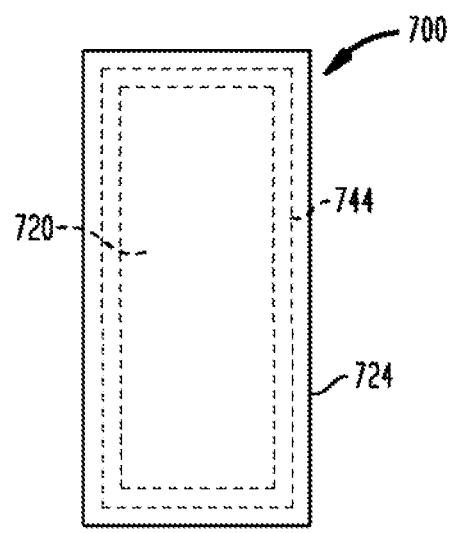

FIGS. 7A and 7B are schematic illustrations of another embodiment of an anchorage device. An anchorage device 700 includes a mesh substrate 724 that can be formed with one or more sheets of mesh material that can be sealed along a portion of a perimeter of the substrate 724 or can be formed from a single sheet of mesh material as described above for previous embodiments. The mesh substrate 724 also defines a pocket 744 that can receive an implantable medical device 720 therein as shown in FIG. 7B. The mesh substrate 724 can be formed with, for example, a non-biodegradable material or a non-resorbable material and includes pores (not shown) that can be sized similar to or the same as described above for previous embodiments.

In this embodiment, the mesh substrate 724 is formed with a flexible shape-memory material that allows the anchorage device 700 to be moved between a biased collapsed configuration (shown in FIG. 7A) to an expanded configuration when an implantable medical device 720 is disposed within the pocket 744 of the anchorage device 700. The anchorage device 700 and implantable medical device 720 can be implanted within a patient and when the treatment is completed, the implantable medical device 720 can be removed from the anchorage device 700. After the implantable medical device 720 is removed from the anchorage device 700, the anchorage device 700 can assume its biased collapsed configuration (shown in FIG. 7A). As the anchorage device 700 moves from its expanded configuration to its collapsed configuration, a portion or portions of the substrate 724 can pull away and detach from surrounding tissue to aid in the removal of the anchorage device 700.

In some embodiments, the shape memory material used to form the mesh substrate 724 can be affected by changes in temperature. For example, the anchorage device 700 can be moved from the expanded configuration to the collapsed configuration when the mesh substrate 724 is exposed to a predetermined threshold temperature. When the implantable medical device 720 is removed from the anchorage device 700, the anchorage device 700 can be moved to its collapsed configuration after the mesh substrate 724 reaches a threshold temperature.

In another example embodiment of an anchorage device, the anchorage device can be used as a hemostats to, for example, stop the flow of blood at a surgical site and/or speed the blood clotting process at a surgical site. In some embodiments, for example, an anchorage device as described herein can include a mesh substrate as described above for previous embodiments that can be used as a hemostats. In some embodiments, the mesh substrate can include one side or sheet of mesh material that is coated with a hemostatic agent such as, for example, oxidized regenerated cellulose, chitosan, surgicel, oxycel, gel foam, Spongostan®, Surgifoam®, Avitene, thrombin, Ostene®, or other suitable hemostatic agent. In such an embodiment, the other side or sheet of mesh material can optionally be coated with a biodegradable polymer.

In some such embodiments, the hemostatic side can be coated with, for example, a polyarylate and can include one or more APIs, such as those disclosed herein. In other embodiments, the hemostatic side is coated with a polymer and one or both of rifampin and/or minocycline. In some such embodiments, the other side (the side not coated with a hemostatic agent) can be coated with, for example, polyarylate and can include a drug or drug combination, such as, for example, Rifampin and Minocycline. In some such embodiments, both the hemostatic side and the other side can be coated with, for example, polyarylate and can include a drug or drug combination, such as, for example, Rifampin and Minocycline. In some such embodiments, neither the side with the hemostatic agent or the other side are coated with polyarylate.

In some embodiments, both sides of the substrate can be coated with a hemostatic agent. In such an embodiment, one or both of the sides can optionally be coated with a biodegradable polymer, such as, for example, polyarylate, and can include, a drug or drug combination, such as, for example, Rifampin and Minocycline. In some embodiments, one or both sides of the substrate can first be coated with a biodegradable polymer and then coated with a hemostatic agent. Although polyarylate, Rifampin, and Minocycline are described in these examples, it should be understood that other polymers and/or APIs could alternatively be used.

To illustrate the kinetics of drug release, in one example procedure a piece of mesh 1.3 cm×2 cm was placed in 10 mL of phosphate buffered saline in a 20 Ml scintillation vial. The vial was placed in a 37° C. incubator shaker. At periodic intervals, the buffer was removed and analyzed by Reversed phase HPLC for Rifampin and Minocycline. At each sampling point, fresh buffer was added. The cumulative % Drug released was calculated and plotted as a function of time as shown in the graphs of FIGS. 8A, 8B and 8C. Three types of devices were used in this study, as shown in Table 1 below and in FIGS. 8A, 8B and 8C. The Tyrosine Polyarylate used in this example was as follows: Poly (72.5% desaminotyrosyl tyrosine ethyl ester co 27.5% desaminotyrsyl tyrosine ethyl ester succinate). The antibiotic used in this example was as follows: antibiotics=Rifampin and Minocycline HCl.

TABLE 1

| | Base device | Modification | Coating | Composition of patch | Amt of Rifampin and Minocycline in coating solution | Amt of Rifampin and Minocycline in patch |
|---|---|---|---|---|---|---|
| 1 | Polypropylene mesh | | Polyarylate with Rifampin and Minocycline | — | 1.2% of Minocycline 0.9% of Rifampin by weight | — |
| 2 | Polypropylene mesh with a hole cut in the center | a hole cut in the center (about 20% of area) | Polyarylate with Rifampin and Minocycline | — | 1.2% of Minocycline 0.9% of Rifampin by weight | — |
| 3 | Polypropylene mesh with a hole and a patch | with a hole cut in the center (about 20% of area) and the hole was patched | Polyarylate with Rifampin and Minocycline | tyrosine polyarylate film containing Rifampin and Minocycline | 1.2% of Minocycline 0.9% of Rifampin by weight | 3.2% of Minocycline 2.2% of Rifampin by weight |

The tensile modulus of various devices described in Table 2 below was determined by Dynamic Mechanical Analysis, using a TA instruments RSA-III DMA. Testing parameters were as follows: (a) Device size: 13 mm×10 mm; Temp: Ambient, the sample is stretched at 0.3 mm/min for 3 min; (b) Tensile Modulus of Tissue (Literature) (2.5 lbs/inch) (c) Two kinds of meshes were used.

For item 2 in Table 2 below, cutting a large hole caused a large drop in the modulus. However, since the initial modulus was far greater than tissue, this decrease did not impact the clinical usefulness of the materials.

For item 3 in Table 2 below, to simulate holes that are intermediate in size, the knots between strands were cut. In this example, 2 knots were cut. This effectively made the pore size of surrounding the cuts 4 times that of the uncut mesh. In this case, the modulus decreased by less than 50%.

TABLE 2

| | Base device polypropylene | Modification | Coating | Patch | Antibiotics in Coating Solution | Antibiotics in Patch | Youngs Modulus (kPA) | Modulus > Tissue |
|---|---|---|---|---|---|---|---|---|
| 1 | Stiff | | | — | | — | 7000 | Yes |
| 2 | Stiff | Large hole cut in center (20%) and hole was patched | | — | | — | 600 | Yes |
| 3 | Stiff | 2 small "holes" created by cutting 2 mesh knots | | — | | — | 4300 | Yes |
| 4 | Soft | | Polyarylate with antibiotics | — | 1.2% of Minocycline 0.9% of Rifampin by weight | | 1000 | Yes |
| 5 | Soft | Large hole cut in center (20%) | Polyarylate with antibiotics | — | 1.2% of Minocycline 0.9% of Rifampin by weight | — | 50 | Yes |
| 6 | Soft | 2 small "holes" created by cutting 2 mesh knots | Polyarylate with antibiotics | | 1.2% of Minocycline 0.9% of Rifampin by weight t | | 130 | Yes |
| 7 | Soft | Large hole cut in center (20%) | Polyarylate with antibiotics | Polyarylate with antibiotics | 1.2% of Minocycline 0.9% of Rifampin by weight | 3.2% of Minocycline 2.2% of Rifampin by weight | 19000 | Yes |
| 8 | Soft | 2 small "holes" created by cutting 2 mesh knots | Polyarylate with antibiotics | Polyarylate with antibiotics | 1.2% of Minocycline 0.9% of Rifampin by weight | 3.2% of Minocycline 2.2% of Rifampin by weight | 50000 | Yes |

The Tyrosine Polyarylate used in these examples was as follows: Poly (72.5% desaminotyrosyl tyrosine ethyl ester co 27.5% desaminotyrsyl tyrosine ethyl ester succinate). The antibiotic used in these examples was as follows: antibiotics=Rifampin and Minocycline HCl.

For the examples of items 4-8, a coated mesh was used. A very soft mesh, with an initial modulus 15% of the stiff mesh was used in the example of item 5 above. Once again, a larger decrease in modulus was seen with a single large pore as compared to 2 small pores, as shown for item 6 above. However, the decrease in modulus can easily be compensated by "patching" the hole with a film. In this, a degradable film whose composition was the same as that used for the coating was used. As can be seen in items 7 and 8; the tensile modulus shows a large increase compared to even the original coated mesh. Thus, a pore size and configuration can be selected to suit any required clinical need and by applying either a coating or a patch, the mechanical properties can be adjusted to match.

Example 1

Figure 9:
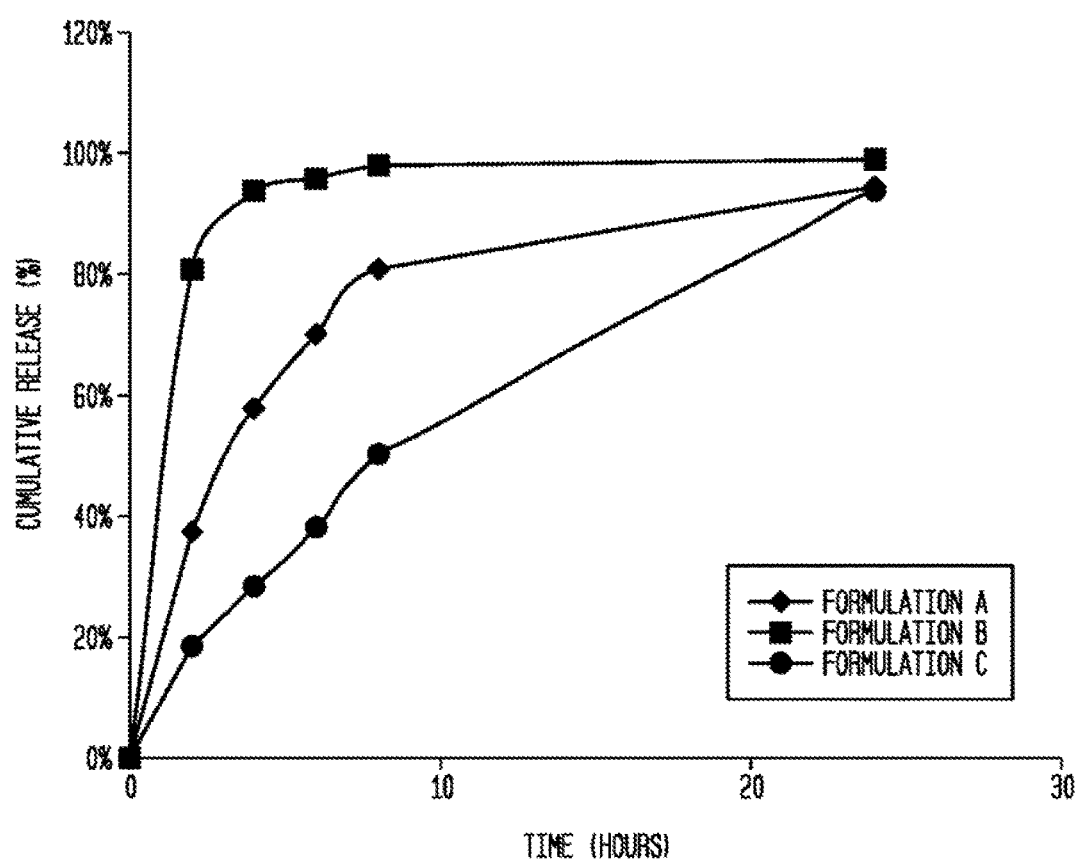
FIG. 9 is a graph showing the cumulative release of minocycline and rifampin.

FIG. 9, and Table 3 below, shows the cumulative release of rifampin and minocycline from three formulations (Formulation A, Formulation B, and Formulation C). The mesh substrate used here is a fully resorbable terpolymer of glycolic acid 6-hydroxycaproic acid and 1-3 propanediol. The total weight of the drug would range from about 5 mg to about 50 mg for Rifampin and about 5 mg to about 20 mg for Minocycline HCl. This is to keep, it is believed, the maximum drug that can be released in 1 day to a maximum of 1/10 of the oral daily dose. This low dose is sufficient for the product to be efficacious, since the drug is delivered locally at the site of action. This results in high tissue concentrations, which are above the minimum inhibitory concentrations of common pathogens. In some embodiments, the amount of each of rifampin and minocyclin in the devices of FIG. 9 comprise from about 0.85 to about 1.20 micrograms/cm2.

TABLE 3

| | Cumulative Release (%) | | |
|---|---|---|---|
| Time (h) | FORMULATION A | FORMULATION B | FORMULATION C |
| 0 | 0 | 0 | 0 |
| 2 | 37 (30 to 40) | 81 | 18 |
| 4 | 58 (50 to 60) | 94 | 28 |
| 6 | 70 (65 to 75) | 96 | 38 |
| 8 | 81 (75 to 85) | 98 | 50 |
| 24 | 95 (>90) | 99 | 94 |

Example 2

Standard in vitro studies were conducted to demonstrate effectiveness against several pathogenic organisms.

Minimum Inhibitory Concentrations

Establishing the MIC of antimicrobials is a necessary step in the process of establishing effective use concentrations. Approved standards for this activity with antibiotics are published by NCCLS. These standards are primarily intended for use in clinical settings with patient isolates. However, they represent a consensus methodology for best practice in determining MICS that are reproducible and defensible. The principles upon which they are based provide a sound framework for determining the MIC for the test.

Materials:

The broth dilution method was used to measure quantitatively the in vitro activity of an antimicrobial agent against a given microbial isolate. To perform the test, a series of tubes were prepared with a broth to which various concentrations of the antimicrobial agent were added. The tubes were then inoculated with a standardized suspension of the test organism. After incubation the tubes were examined and the minimal inhibitory concentration (MIC) was determined.

The following organism were used: *Acinetobacter baumanii* A TCC 19606; *Staphylococcus epidermidis* A TCC 14990; *Staphylococcus aureus* ATCC 6538; Methicillin-resistant *Staphylococcus aureus* ATCC 33591; *Escherichia coli* ATCC 8739; *Staphylococcus capitis* ATCC 35661; or *Staphylococcus schleiferi* ATCC 43808.

Results:

TABLE 4

| | Minimum Inhibitory Concentration (microgram/mL) | |
|---|---|---|
| Test Organism | Minocycline | Rifampin |
| S. aureus | 0.017 | 0.016 |
| S. epidermidis | 0.017 | 0.016 |
| E. coli | 2.233 | 2.057 |
| MRSA | 2.233 | 2.057 |
| A. baumanii | 0.140 | 0.129 |
| S. capitis | 0.017 | 0.016 |
| S. sclefeifreii | 0.017 | 0.016 |

The device is effective against each of these organisms.

The AATCC (American Association of Textile Chemists and Colorists) 100 test method was designed to quantitatively test the ability of fabrics and textiles to inhibit the growth of microorganisms or kill them, over a 24 hour period of contact. TYRX, Inc modified the test to test at additional time points of 48 and 72 h to show continuing efficacy against the organisms.

Summary of the AATCC 100 Test Method:
1. The test microorganism were grown in liquid culture.
2. The concentration of the test microorganism as standardized.
3. The microbial culture as diluted in a sterile nutritive solution.
4. Control and test fabric swatches were inoculated microorganisms.
5. The inoculation was performed such that the microbial suspension touched only the fabric (see actual method for details).
6. Bacteria levels on both control and test fabrics were determined at "time zero" by elution in a large volume of neutralizing broth, followed by dilution and platin.
7. A control was run to verify that the neutralization/elution method effectively neutralized the antimicrobial agent in the fabric.
8. Additional inoculated control and test fabrics were allowed to incubate, undisturbed in sealed jars, for 24 hours.
9. After incubation, microbial concentrations were determined.
10. Reduction of microorganisms relative to initial concentrations and the control fabric, was calculated.

Strengths of the AATCC 100 Test Method:
1. The method was quantitative and results tended to be reproducible.
2. The method tested for both bacteriostatic (growth-inhibiting) and bactericidal (bacteria-killing) properties.
3. Microbial concentrations were standardized, and bacteria were provided with nutrients during the incubation period, which provided them with ample opportunity to grow if fabrics weren't sufficiently antimicrobial. This is in contrast to certain other antimicrobial tests, where microbes were "incubated" in non-nutritive suspensions, which itself may be stressful over long periods.

Summary of Results From AATCC Testing (Fully Degradable Mesh Made from Terpolymer of Glycolic Acid, Hydroxycaproic Acid or 1-3 Propylene Diol):

TABLE 5

| | Initial Innoculum | Log Reduction in Bacterial Counts | | |
|---|---|---|---|---|
| Test Organism | (CFU/mL) | 24 h | 48 h | 72 h |
| S. aureus | $5.15 \times 10^6$ | $10^4$ | $10^4$ | $10^4$ |
| S. epidermidis | $3.35 \times 10^6$ | $10^4$ | $10^4$ | $10^4$ |
| E. coli | $6.75 \times 10^6$ | $10^4$ | $10^4$ | $10^4$ |
| MRSA | $6.00 \times 10^6$ | $10^4$ | $10^4$ | $10^4$ |
| A. baumanii | $6.90 \times 10^6$ | $10^4$ | $10^4$ | $10^4$ |
| E. aerogenes | $3.65 \times 10^6$ | $10^4$ | $10^4$ | $10^4$ |
| P. mirabilis | $1.85 \times 10^6$ | $10^4$ | $10^4$ | $10^4$ |
| S. capitis | $1.28 \times 10^6$ | $10^4$ | $10^3$ | $10^3$ |
| S. sclefeifreii | $2.6 \times 10^6$ | $10^5$ | $10^5$ | $10^4$ |

Summary of Results From AATCC Testing For Device Type 1 (Partly Degradable—Underlying Mesh is Polypropylene):

TABLE 6

| | Initial Innoculum | Log Reduction in Bacterial Counts | | |
|---|---|---|---|---|
| Test Organism | (CFU/mL) | 24 h | 48 h | 72 h |
| S. aureus | $2.31 \times 10^6$ | $10^4$ | $10^4$ | $10^4$ |
| S. epidermidis | $1.5 \times 10^6$ | $10^4$ | $10^4$ | $10^4$ |
| E. coli | $1.34 \times 10^6$ | $10^3$ | $10^3$ | $10^2$ |
| MRSA | $3.23 \times 10^6$ | $10^4$ | $10^4$ | $10^4$ |
| A. baumanii | $2.81 \times 10^7$ | $10^5$ | $10^5$ | $10^5$ |
| E. aerogenes | $1.67 \times 10^7$ | $10^4$ | $10^5$ | $10^5$ |
| P. mirabilis | $1.21 \times 10^7$ | $10^5$ | $10^5$ | $10^5$ |
| S. sclefeifreii | $6.40 \times 10^7$ | $10^3$ | $10^3$ | $10^3$ |

Example 4

Tissue Concentration

In some embodiments, the antibiotic is minocycline and a tissue concentration of the minocycline is between about 0.65 µg/mL and 0.8 µg/mL after about 2 hours; where the tissue concentration of the minocycline is between about 2.55 µg/mL and about 2.75 µg/mL after about 6 hours; and where the tissue concentration of the minocycline is between about 1.2 μg/mL and about 1.9 μg/mL after about 24 hours. In other embodiments, the antibiotic is rifampin and a tissue concentration of the rifampin is between about 0.6 μg/mL and 1.4 μg/mL after about 2 hours; where the tissue concentration of the rifampin is between about 1.9 μg/mL and about 2.3 μg/mL after about 6 hours; and where the tissue concentration of the rifampin is between about 2.6 μg/mL and about 4.2 μg/mL after about 24 hours. (See, e.g., Table 7).

Example 5

Pocket Concentration

In some embodiments, the antibiotic is minocycline and a pocket concentration of the minocycline is between about 15 μg/mL and about 17 μg/mL after about 2 hours; and where the pocket concentration of the minocycline is between about 25 μg/mL and about 210 μg/mL after about 6 hours. In other embodiments, the antibiotic is rifampin and a pocket concentration of the rifampin is between about 1 μg/mL and about 20 μg/mL after about 2 hours; and where the tissue concentration of the rifampin is between about 15 μg/mL and about 110 μg/mL after about 6 hours. (See, e.g., Table 8).

Example 6

Post Implant Serum Concentration

In some embodiments, the antibiotic is minocycline and a pocket concentration of the minocycline is between about 0.03 μg/mL and about 0.06 μg/mL after about 2 hours; where the pocket concentration of the minocycline is between about 0.06 μg/mL and about 0.1 μg/mL after about 6 hours; and where the tissue concentration of the minocycline is between about 0.05 μg/mL and about 0.09 μg/mL after about 24 hours. In other embodiments, the antibiotic is rifampin and a pocket concentration of the rifampin is between about 0.015 μg/mL and about 0.045 μg/mL after about 2 hours; where the tissue concentration of the rifampin is between about 0.01 μg/mL and about 0.04 μg/mL after about 6 hours; and where the tissue concentration of the rifampin is between about 0.03 μg/mL and about 0.06 μg/mL after about 24 hours. (See, e.g., Table 9).

TABLE 7

| Average Tissue concentration (μg/mL) | | |
| --- | --- | --- |
| time | Left | Right |
| Minocycline | | |
| 2 h | 0.70 | 0.783 |
| 6 h | 2.685 | 2.603 |
| 24 h | 1.328 | 1.842 |
| Rifampin | | |
| 2 h | 0.765 | 1.27 |
| 6 h | 2.075 | 2.21 |
| 24 h | 4.045 | 2.72 |

TABLE 8

| Pocket concentration (μg/mL) | | |
| --- | --- | --- |
| time | Left | Right |
| Minocycline | | |
| 2 h | 16.4 | n/a |
| 6 h | 26.8 | 207 |
| 24 h | n/a | n/a |
| Rifampin | | |
| 2 h | 2.02 | 16.4 |
| 6 h | 19.6 | 100 |
| 24 h | n/a | n/a |

TABLE 9

| Post implant Serum concentration (μg/mL) | |
| --- | --- |
| time | |
| | Minocycline |
| 2 h | 0.0465 |
| 6 h | 0.0791 |
| 24 h | 0.0694 |
| | Rifampin |
| 2 h | 0.0271 |
| 6 h | 0.0208 |
| 24 h | 0.0443 |

In some embodiments of an anchorage device as described herein, a layer of film can be embedded between 2 sheets of mesh that are ultrasonically sealed along their borders (film itself is not attached to the mesh). In some embodiments, ultrasonically sealed sheets of mesh can act as a temporary or permanent "envelope" for film depending on the application.

In one example use of an anchorage device for soft tissue repair can include a mesh substrate that can be polypropylene on one side and resorbable on the other as described herein. In some embodiments, multiple films loaded with different actives can be embedded inside an anchorage device. For example, the multiple films can be placed inside an envelope or pocket of a mesh substrate. In some embodiments, an anchorage device can include Teflon on one side and any mesh material on the other side with a film or films disposed in between. In some embodiments, an anchorage device can be totally resorbable, for example, if used to help in breast implant insertion/inguinal applications.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combinations of components, other embodiments are possible having any combination or sub-combination of any features and/or components from any of the embodiments described herein. The specific configurations of the various components can also be varied. For example, the size and specific shape of the various components can be different than the embodiments shown, while still providing the functions as described herein.

For example, any of the embodiments of an anchorage device (e.g., 100, 200, 300, 400, 500, 600, 700) can include a biodegradable and/or resorbable polymer coating (e.g., 126) disposed on at least a portion of the mesh substrate (e.g., 124, 224, 324, 424, 524, 624, 724). In another example, any of the embodiments of a mesh substrate (e.g., 124, 224, 324, 424, 524, 624, 724) can be formed with one or more sheets of mesh material by heat, ultrasonically, bonding, knitting, or any suitable method used for surgical mesh.

In addition, it should be understood that the anchorage devices (e.g., 100, 200, 300, 400, 500, 600, 700) described herein can be used to support a variety of different types of implantable medical devices and/or to support a variety of different types of tissue. In addition, the anchorage devices (e.g., 100, 200, 300, 400, 500, 600, 700) and methods described herein can be used for a variety of different types of medical treatments in a variety of different locations in a body of a patient.

The invention claimed is:

1. An anchorage device comprising a mesh substrate coupled to an implantable medical device, said mesh substrate comprising two sheets that define a pocket, said implantable medical device being positioned in said pocket, said mesh substrate having a coating comprising a polymer and at least one active pharmaceutical ingredient;
wherein said mesh substrate comprises pores ranging in size between about 5 mm to about 10 mm,
wherein said mesh substrate comprises one or more apertures,
wherein said apertures are larger than said pores,
wherein one of said sheets is formed with a non-biodegradable material and one of said sheets is formed with a biodegradable material, and
wherein said sheet that is formed with said non-biodegradable material has no pores.

2. The anchorage device of claim 1, wherein said active pharmaceutical ingredient is selected from the group consisting of anesthetics, antibiotics, anti-inflammatory agents, procoagulant agents, fibrosis-inhibiting agents, anti-scarring agents, leukotriene inhibitors/antagonists, cell growth inhibitors and mixtures thereof.

3. The anchorage device of claim 1, wherein said active pharmaceutical ingredient is an antibiotic.

4. A method of preventing, mitigating, or treating a bacterial infection comprising implanting the anchorage device of claim 3.

5. The method of claim 3, wherein said antibiotic is effective against *S. aureus, S. epidermidis, E. coli*, MRSA, *A. baumanii, E. aerogenes, P. mirabilis, S. capitis*, and *S. sclefeifreii*.

6. The anchorage device of claim 1, wherein said antibiotic is selected from the group consisting of rifampin and minocycline and mixtures thereof.

7. The anchorage device of claim 1, wherein said polymer is selected from the group consisting of polylactic acid, polyglycolic acid, poly(L-lactide), poly(D,L-lactide) polyglycolic acid[polyglycolide], poly(L-lactide-co-D,L-lactide), poly(L-lactide-co-glycolide), poly(D, L-lactide-co-glycolide), poly(glycolide-co-trimethylene carbonate), poly (D,L-lactide-co-caprolactone), poly(glycolide-co-caprolactone), polyethylene oxide, polydioxanone, polypropylene fumarate, poly(ethyl glutamate-co-glutamic acid), poly(tert-butyloxy-carbonylmethyl glutamate), poly-caprolactone, polycaprolactone co-butylacrylate, polyhydroxybutyrate, copolymers of polyhydroxybutyrate, poly (phosphazene), poly(phosphate ester), poly(amino acid), polydepsipeptides, maleic anhydride copolymers, polyiminocarbonates, poly[(97.5% dimethyl-trimethylene carbonate)-co-(2.5% trimethylene carbonate)], poly(orthoesters), tyrosine-derived polyarylates, tyrosine-derived polycarbonates, tyrosine-derived polyiminocarbonates, tyrosine-derived polyphosphonates, polyethylene oxide, polyethylene glycol, polyalkylene oxides, hydroxypropylmethylcellulose, polysaccharides such as hyaluronic acid, chitosan and regenerate cellulose.

8. The anchorage device of claim 1, wherein said polymer is a polyarylate.

9. The anchorage device of claim 1, wherein said polymer is a member of the P22-xx family.

10. The anchorage device of claim 9, wherein said polymer comprises 10-30% DT.

11. The anchorage device of claim 1, wherein said active pharmaceutical ingredient is released from said coating over about a 24 hour time period.

12. The anchorage device of claim 1, wherein said polymer is a polyarylate and said active pharmaceutical ingredient is selected from an antibiotic.

13. The anchorage device of claim 12, wherein said polymer is selected from the group consisting of a tyrosine-derived polyarylate and said antibiotic is selected from the group consisting of rifampin, minocycline, or mixtures thereof.

14. The anchorage device of claim 1, wherein said implantable medical device is a cardiovascular implantable electronic device and wherein said active pharmaceutical ingredient is an antibiotic.

15. The anchorage device of claim 14, wherein said antibiotic achieves a level equal or exceeding a minimum inhibitory concentration of said antibiotic for methicillin-resistant *Staphylococcus aureus* on both sides of said cardiovascular implantable electronic device for at least about 24 hours after implantation of said cardiovascular implantable electronic device.

16. The anchorage device of claim 14, wherein said antibiotic achieves a level equal or exceeding a minimum inhibitory concentration of said antibiotic for methicillin-resistant *Staphylococcus aureus* on both sides of said cardiovascular implantable electronic device for at least about hours after implantation of said cardiovascular implantable electronic device.

17. The anchorage device of claim 1, wherein said mesh covers only a portion of said implantable medical device.

18. The anchorage device of claim 1, wherein said mesh is formed by knitting.

19. The anchorage device of claim 1, wherein said mesh has a low areal density.

20. The anchorage device of claim 1, wherein an amount of said active pharmaceutical ingredient in said coating ranges from between about 5% to about 30% by total weight of said coating.

21. The anchorage device of claim 1, wherein said coating has a thickness ranging from about 5 μm to about 200 μm.

22. The anchorage device of claim 1, wherein said one or more apertures are covered or coated with a polymer.

23. The anchorage device of claim 1, wherein said one or more apertures allow for tissue ingrowth.

24. The anchorage device of claim 1, wherein said active pharmaceutical ingredient is a combination of rifampin and minocycline.

25. The anchorage device of claim 1, wherein said anchorage device is entirely resorbable.

26. The anchorage device of claim 1, wherein said mesh substrate is resorbable.

27. The anchorage device of claim 1, wherein said polymer comprises a resorbable material.

28. The anchorage device of claim 27, wherein said resorbable material comprises a resorbable polyarylate.

29. The anchorage device of claim 27, wherein said resorbable material is selected from a group consisting of: BTE glutarate, DTM glutarate, DT propylamide glutarate, DT glycineamide glutarate, BTE succinate, BTM succinate, BTE succinate PEG, BTM succinate PEG, DTM succinate PEG, DTM succinate, DT N-hydroxysuccinimide succinate, DT glucosamine succinate, DT glucosamine glutarate, DT PEG ester succinate, DT PEG amide succinate, DT PEG ester glutarate, DT PEG ester succinate, DTMB P(Desaminotyrsoyl tyrosine methylparaben ester-glutarate), and DTPP P(Desaminotyrsoyl tyrosine propylparaben ester-glutarate).

30. The anchorage device of claim 27, wherein said resorbable material is a fully resorbable terpolymer of glycolic acid 6-hydroxycaproic acid and 1,3 propanediol.

31. The anchorage device of claim 1, wherein said mesh substrate comprises filaments that define said pores therebetween.

32. The anchorage device of claim 1, wherein a portion of said implantable medical device extends outside of said pocket.

33. The anchorage device of claim 1, wherein said pocket is defined as an area about 1 inch around said implantable medical device in all dimensions.

34. The anchorage device of claim 1, wherein a portion of a side along said perimeter is not sealed such that an opening is defined though which said implantable medical device can be inserted into said pocket.

35. An anchorage device comprising a mesh substrate coupled to an implantable medical device, said mesh substrate comprising two sheets that define a pocket, said implantable medical device being positioned in said pocket, said mesh substrate comprising a plurality of filaments that define pores therebetween, said mesh substrate having a coating comprising a polymer and at least one active pharmaceutical ingredient;
wherein said mesh substrate comprises one or more apertures wherein said apertures are larger than said pores,
wherein one of said sheets is formed with a non-resorbable material and one of said sheets is formed with a resorbable material, and
wherein said sheet that is formed with said non-resorbable material has no pores.

36. The anchorage device of claim 35, wherein a portion of said implantable medical device extends outside of said pocket.

37. The anchorage device of claim 35, wherein said pocket is defined as an area about 1 inch around said implantable medical device in all dimensions.

38. The anchorage device of claim 35, wherein a portion of a side along said perimeter is not sealed such that an opening is defined though which said implantable medical device can be inserted into said pocket.

39. An anchorage device comprising:
a mesh substrate coupled to an implantable medical device, said mesh substrate having a coating comprising a polymer and at least one active pharmaceutical ingredient,
wherein said mesh substrate comprises two sheets that are sealed along a portion of a perimeter of said mesh substrate to define a pocket, said implantable medical device being positioned in said pocket,
wherein said mesh substrate comprises one or more pores and one or more apertures, said apertures being larger than said pores,
wherein one of said sheets is formed with a non-biodegradable material or a non-resorbable material and one of said sheets is formed with a biodegradable material or a resorbable material, and
wherein said sheet that is formed with said non-biodegradable material or said non-resorbable material has no pores.

40. The anchorage device of claim 39, wherein a portion of a side along said perimeter is not sealed such that an opening is defined though which said implantable medical device can be inserted into said pocket.

41. The anchorage device of claim 39, wherein said sheets are ultrasonically sealed along said portion of said perimeter.

42. The anchorage device of claim 39, wherein said apertures are formed in each of said sheets.

43. The anchorage device of claim 39, wherein said apertures are formed in only one of said sheets.

44. The anchorage device of claim 39, wherein said coating covers said apertures.

45. The anchorage device of claim 39, wherein said pocket has a substantially toroidal or donut shape.

46. The anchorage device of claim 39, further comprises a layer of film embedded between said sheets.

47. The anchorage device of claim 39, wherein said polymer is a tyrosine-derived polyarylate.

48. The anchorage device of claim 39, wherein said at least one active pharmaceutical ingredient is a combination of rifampin and minocycline.

49. The anchorage device of claim 39, wherein said coating has a thickness ranging from about 5 μm to about 200 μm.

50. The anchorage device of claim 39, wherein said coating has a thickness of about 10 μm.

* * * * *